(12) United States Patent
Salman et al.

(10) Patent No.: US 7,446,123 B2
(45) Date of Patent: Nov. 4, 2008

(54) AZABICYCLO DERIVATIVES AS MUSCARINIC RECEPTOR ANTAGONISTS

(75) Inventors: Mohammad Salman, Plainsboro, NJ (US); Anita Mehta, Plainfield, IL (US); Pakala Kumara Savithru Sarma, Haryana (IN); Naresh Kumar, Haryana (IN); Sankaranarayanan Dharmarajan, Haryana (IN); Kirandeep Kaur, Haryana (IN); Anita Chugh, Delhi (IN)

(73) Assignee: Ranbaxy Laboratories Limited, Gurgaon, Haryana (IN)

( * ) Notice: Subject to any disclaimer, the term of this patent is extended or adjusted under 35 U.S.C. 154(b) by 0 days.

(21) Appl. No.: 10/552,455

(22) PCT Filed: Jan. 7, 2004

(86) PCT No.: PCT/IB2004/000012

§ 371 (c)(1),
(2), (4) Date: Jan. 14, 2008

(87) PCT Pub. No.: WO2004/089364

PCT Pub. Date: Oct. 21, 2004

(65) Prior Publication Data

US 2006/0287380 A1  Dec. 21, 2006

(30) Foreign Application Priority Data

Apr. 11, 2003  (WO) ....................... PCT/IB03/01367

(51) Int. Cl.
*A61K 31/40* (2006.01)
*A61K 31/4035* (2006.01)
*C07D 209/52* (2006.01)
*C07D 209/52* (2006.01)

(52) U.S. Cl. ..................... 514/412; 548/452; 548/470; 548/515; 514/416

(58) Field of Classification Search ................. 548/452, 548/515, 470; 514/412, 416
See application file for complete search history.

(56) References Cited

U.S. PATENT DOCUMENTS

| | | | | |
|---|---|---|---|---|
| 2,490,714 | A | 12/1949 | Searle | 260/239 |
| 3,176,019 | A | 3/1965 | Campbell et al. | 260/293.4 |
| 5,001,160 | A | 3/1991 | McPherson et al. | 514/255 |
| 5,164,402 | A | 11/1992 | Brighty | 514/300 |
| 5,179,108 | A | 1/1993 | George et al. | 514/319 |
| 5,281,601 | A | 1/1994 | Cross et al. | 514/320 |
| 5,397,800 | A | 3/1995 | Alker et al. | 514/413 |
| 5,948,792 | A * | 9/1999 | Tsuchiya et al. | 514/317 |
| 6,130,232 | A * | 10/2000 | Mase et al. | 514/318 |
| 6,174,900 | B1 * | 1/2001 | Okada et al. | 514/317 |
| 6,313,312 | B1 | 11/2001 | Banks et al. | 548/452 |
| 7,232,835 | B2 | 6/2007 | Mehta et al. | 514/323 |
| 7,288,562 | B2 | 10/2007 | Mehta et al. | |
| 2003/0105071 | A1 | 6/2003 | Cuny et al. | 514/210.2 |
| 2003/0162780 | A1 | 8/2003 | Brotherton-Pleiss et al. | 514/235.5 |
| 2003/0171362 | A1 | 9/2003 | Madera et al. | 514/218 |
| 2006/0247225 | A1 | 11/2006 | Mehta et al. | |
| 2006/0281805 | A1 | 12/2006 | Mehta et al. | |
| 2007/0010568 | A1 | 1/2007 | Mehta et al. | |
| 2007/0135508 | A1 | 6/2007 | Mehta et al. | |

FOREIGN PATENT DOCUMENTS

| | | |
|---|---|---|
| CA | 2155320 | 8/1993 |
| EP | 0 325 571 | 7/1989 |
| EP | 0 388 054 | 9/1990 |
| EP | 0 413 455 | 2/1991 |
| EP | 0 613 232 | 8/1994 |
| EP | 0 801 067 | 10/1997 |
| EP | 0 823 423 | 2/1998 |
| EP | 0 863 141 | 9/1998 |
| GB | 940540 | 10/1963 |
| JP | 92921/1994 | 4/1994 |
| JP | 135958/1994 | 5/1994 |
| WO | WO 91/09013 | 6/1991 |
| WO | WO 93/16018 | 8/1993 |
| WO | WO 93/16048 | 8/1993 |
| WO | WO 96/33973 | 10/1996 |
| WO | WO 97/45414 | 12/1997 |
| WO | WO 98/05641 | 2/1998 |
| WO | WO 98/29402 | 7/1998 |
| WO | WO 98/53814 | 12/1998 |
| WO | WO 99/43657 | 9/1999 |
| WO | WO 01/42212 | 6/2001 |
| WO | WO 01/42213 | 6/2001 |

(Continued)

OTHER PUBLICATIONS de Groat and Yoshimura, "Pharmacology of the Lower Urinary Tract", *Annual Review of Pharmacology and Toxicology*, 41:691-721 (2001).
Cheng and Prusoff, "Relationship between the inhibition constant ($K_1$) and the concentration of inhibitor which causes 50 per cent inhibition ($I_{50}$) of an enzymatic reaction", *Biochemical Pharmacology*, 22:3099-3108 (1973).
Birdsall et al., "Muscarinic receptors: it's a knockout", *Trends in Pharmacological Sciences*, 22(5):215-219 (2001).
Brighty et al., "Synthesis of (1α,5α,6α)-6-Amino-3-azabicyclo[3.1.0]hexane, a Novel Achiral Diamine", *Synlett*, 1097-1099 (1996).
Braish et al., "Construction of the (1α,5α,6α)-6-Amino-3-azabicyclo[3.1.0]hexane Ring System", *Synlett*, 1100-1102 (1996).
Chapple, "Muscarinic receptor antagonists in the treatment of overactive bladder", *Urology*, 55(Suppl. 5A):33-46 (2000).

(Continued)

*Primary Examiner*—Golam M Shameem
(74) *Attorney, Agent, or Firm*—Jay R. Deshmukh, Esq.; George E. Heibel, Esq.

(57) ABSTRACT

This invention generally relates to muscarinic receptor antagonists of formula (I) which are useful, among other uses for the treatment of various diseases of the respiratory, urinary and gastrointestinal systems mediated through muscarinic receptors. The invention also relates to pharmaceutical compositions containing the compounds of the present invention and the methods of treating the diseases mediated through muscarinic receptors.

2 Claims, No Drawings

FOREIGN PATENT DOCUMENTS

| WO | WO 01/47893 | 7/2001 |
|---|---|---|
| WO | WO 01/90081 | 11/2001 |
| WO | WO 01/090082 | 11/2001 |
| WO | WO 02/00652 | 1/2002 |
| WO | WO 02/04402 | 1/2002 |
| WO | WO 02/06241 | 1/2002 |
| WO | WO 02/51841 | 7/2002 |
| WO | WO 02/53564 | 7/2002 |
| WO | WO 03/033495 | 4/2003 |
| WO | WO 03/048124 | 6/2003 |
| WO | WO 03/048125 | 6/2003 |
| WO | WO 2004/004629 | 1/2004 |
| WO | WO 2004/014363 | 2/2004 |
| WO | WO 2004/014853 | 2/2004 |
| WO | WO 2004/018422 | 3/2004 |
| WO | WO 2004/052857 | 6/2004 |
| WO | WO 2004/056767 | 7/2004 |
| WO | WO 2004/056810 | 7/2004 |
| WO | WO 2004/056811 | 7/2004 |
| WO | WO 2004/067510 | 8/2004 |
| WO | WO 2004/069835 | 8/2004 |
| WO | WO 2004/089363 | 10/2004 |
| WO | WO 2004/089898 | 10/2004 |
| WO | WO 2004/089899 | 10/2004 |
| WO | WO 2004/089900 | 10/2004 |
| WO | WO 2005/092341 | 10/2005 |
| WO | WO 2005/003587 | 1/2006 |
| WO | WO 2006/035282 | 4/2006 |
| WO | WO 2006/064304 | 6/2006 |
| WO | WO 2004/005252 | 1/2007 |

OTHER PUBLICATIONS

Eglen et al., "Muscarinic receptor ligands and their theraputic potential", *Current Opinion in Chemical Biology*, 3:426-432 (1999).

Eglen et al., "Theraputic opportunities from muscarinic receptor research", *Trends in Pharmacological Sciences*, 22(8):409-414 (2001).

Felder et al., "Theraputic Opportunities for Muscarinic Receptors in the Central Nervous System", *Journal of Medicinal Chemistry*, 43(23):4333-4353 (2000).

Grover et al., "Chiral Mandelic Acid Template Provides a Highly Practical Solution for (S)-Oxybutynin Synthesis", *Journal of Organic Chemistry*, 65:6283-6287 (2000).

Shacklett and Smith, "The Preparation of Substituted Benzilic Acids", *Journal of the American Chemical Society*, 75:2654-2657 (1953).

Sagara et al., "Cyclohexylmethylpiperidinyltriphenylpropioamide: A Selective Muscarinic $M_3$ Antagonist Discriminating against the Other Receptor Subtypes", *Journal of Medicinal Chemistry*, 45:984-987 (2002).

Nkpa and Chedekel, "Mechanistic Studies on the Addition of Cysteine to 3,4-Dihydroxyphenylalanine", *Journal of Organic Chemistry*, 46:213-215 (1981).

Kadin and Cannon, "Esters of N-Methyl-3-hydroxypiperidine Having Psychotomimetic Activity. II", *Journal of Organic Chemistry*, 27:240-245 (1962).

Broadley and Kelly, "Muscarinic Receptor Agonists and Antagonists", *Molecules*, 6:142-193 (2001).

Moriya et al., "Affinity Profiles of Various Muscarinic Antagonists for Cloned Human Muscarinic Acetylcholine Receptor (mAChR) Subtypes and mAChRs in Rat Heart and Submandibular Gland", *Life Sciences*, 64(25):2351-2358 (1999).

Kubo et al., "Cloning, sequencing and expression of complementary DNA encoding the muscarinic acetylcholine receptor", *Nature*, 323(2):411-416 (1986).

Bonner et al., "Identification of a Family of Muscarinic Acetylcholine Receptor Genes", *Science*, 237:527-531 (1987).

Steers, "The future direction of neuro-urology drug research", *Current Opinion in CPNS Investigational Drugs*, 2(3):268-282.

Steers, Barrot, Wein, "Voiding dysfunction: diagnosis classification and management", In: *Adult and Pediatric Urology*, ed. Gillenwater, Grayhack, Howards, Duckett. Mosby, St. Louis, MO; 1220-1325, 3rd edition (1996).

Weinstock et al., "A General, One-Step Synthesis of α-keto Esters", *Synthetic Communications*, 11(12):943-946 (1981).

Vogel's textbook, "Practical Organic Chemistry" 1046-1047 (5th Ed.).

"Design of prodrugs", ed. H. Bundgaard, Elsevier (1985).

Kaiser et al, "Synthesis and Antimuscarinic Activity of Some 1-Cycloalkyl-1-hydroxy-1-phenyl-3-(4-substituted piperazinyl)-2-propanones and Related Compounds", *Journal of Medicinal Chemistry*, 36(5):610-616 (1993).

Carter et al, "Analogues of Oxybutynin. Synthesis and Antimuscarinic and Bladder Activity of Some Substituted 7-Amino-1-hydroxy-5-heptyn-2-ones and Related Compounds", *Journal of Medicinal Chemistry*, 34(10):3065-3074 (1991).

Morissette et al, "High-throughput crystallization: polymorphs, salts, co-crystals and solvates of pharmaceutical solids", *Advanced Drug Delivery Reviews*, 56:275-300 (2004).

Wess et al., *Life Sciences* (2003) 72:2047:2054.

O'Neil, M., *Drug Discovery Today*, (Oct. 2005) 10(20):1338.

Michael et al., *Naunyn-Schmiedeberg's Arch Pharmacol* (2006) 374:79-85.

Latifpour et al., *The Journal of Pharmacology and Experimental Therapeutics* (1989) 249(1):81-88.

Carrier et al., *The Journal of Pharmacology and Experimental Therapeutics* (1987) 242(2): 531-535.

Ahren et al., *Diabetologia* (1996) 39:383-390.

Abrams et al., *British Journal of Pharmacology* (2006) 148:565-578.

* cited by examiner

AZABICYCLO DERIVATIVES AS MUSCARINIC RECEPTOR ANTAGONISTS

FIELD OF THE INVENTION

This invention generally relates to muscarinic receptor antagonists which are useful, among other uses for the treatment of various diseases of the respiratory, urinary and gastrointestinal systems mediated through muscarinic receptors. The invention also relates to pharmaceutical compositions containing the compounds of the present invention and the methods of treating the diseases mediated through muscarinic receptors.

BACKGROUND OF THE INVENTION

Muscarinic receptors as members of the G Protein Coupled Receptors (GPCRs) are composed of a family of 5 receptor sub-types ($M_1$, $M_2$, $M_3$, $M_4$ and $M_5$) and are activated by the neurotransmitter acetylcholine. These receptors are widely distributed on multiple organs and tissues and are critical to the maintenance of central and peripheral cholinergic neurotransmission. The regional distribution of these receptor sub-types in the brain and other organs has been documented. For example, the $M_1$ subtype is located primarily in neuronal tissues such as cereberal cortex and autonomic ganglia, the $M_2$ subtype is present mainly in the heart where it mediates cholinergically induced bradycardia, and the $M_3$ subtype is located predominantly on smooth muscle and salivary glands (*Nature*, 323, p. 411 (1986); *Science*, 237, p. 527 (1987)).

A review in *Current Opinions in Chemical Biology*, 3, p. 426 (1999), as well as in *Trends in Pharmacological Sciences*, 22, p. 409 (2001) by Eglen et. al., describes the biological potentials of modulating muscarinic receptor sub-types by ligands in different disease conditions, such as Alzheimer's Disease, pain, urinary disease condition, chronic obstructive pulmonary disease, and the like.

A review in *J. Med. Chem.*, 43, p. 4333 (2000), by Felder et. al. describes therapeutic opportunities for muscarinic receptors in the central nervous system and elaborates on muscarinic receptor structure and function, pharmacology and their therapeutic uses.

The pharmacological and medical aspects of the muscarinic class of acetylcholine agonists and antagonists are presented in a review in *Molecules*, 6, p. 142 (2001).

Birdsall et. al. in *Trends in Pharmacological Sciences*, 22, p. 215 (2001) have also summarized the recent developments on the role of different muscarinic receptor subtypes using different muscarinic receptor of knock out mice.

Muscarinic agonists such as muscarine and pilocarpine and antagonists such as atropine have been known for over a century, but little progress has been made in the discovery of receptor subtype-selective compounds, making it difficult to assign specific functions to the individual receptors. Although classical muscarinic antagonists such as atropine are potent bronchodilators, their clinical utility is limited due to high incidence of both peripheral and central adverse effects such as tachycardia, blurred vision, dryness of mouth, constipation, dementia, etc. Subsequent development of the quarterly derivatives of atropine such as ipratropium bromide are better tolerated than parenterally administered options, but most of these are not ideal anti-cholinergic bronchodilators, due to lack of selectivity for muscarinic receptor sub-types, resulting in dose-limiting side-effects such as thirst, nausea, mydriasis and those associated with the heart such as tachycardia mediated by the $M_2$ receptor.

*Annual Review of Pharmacological Toxicol.*, 41, p. 691 (2001), describes the pharmacology of the lower urinary tract infections. Although anti-muscarinic agents such as oxybutynin and tolterodine that act non-selectively on muscarinic receptors have been used for many years to treat bladder hyperactivity, the clinical effectiveness of these agents has been limited due to the side effects such as dry mouth, blurred vision and constipation. Tolterodine is considered to be generally better tolerated than oxybutynin. (Steers et. al., in *Curr. Opin. Invest. Drugs*, 2, 268; Chapple et. al., in *Urology*, 55, 33; Steers et al., *Adult and Pediatric Urology*, ed. Gillenwatter et al., pp 1220-1325, St. Louis, Mo.; Mosby. $3^{rd}$ Edition (1996)).

There remains a need for development of new highly selective muscarinic antagonists which can interact with distinct subtypes, thus avoiding the occurrence of adverse effects.

Compounds having antagonistic activity against muscarinic receptors have been described in Japanese patent application Laid Open Number 92921/1994 and 135958/1994; WO 93/16048; U.S. Pat. No. 3,176,019; GB 940,540; EP 0325 571; WO 98/29402; EP 0801067; EP 0388054; WO 9109013; U.S. Pat. No. 5,281,601. Also, U.S. Pat. Nos. 6,174, 900, 6,130,232 and 5,948,792; WO 97/45414 are related to 1,4-disubstituted piperidine derivatives; WO 98/05641 describes fluorinated, 1,4-disubstitued piperidine derivatives; WO 93/16018 and WO96/33973 are other references of interest. U.S. Pat. No. 5,397,800 discloses 1-azabicyclo[2.2.1] heptanes. U.S. Pat. No. 5,001,160 describes 1-aryl-1-hydroxy-1-substituted-3-(4-substituted-1-piperazinyl)-2-propanones. WO 01/42213 describes 2-biphenyl-4-piperidinyl ureas. WO 01/42212 describes carbamate derivatives. WO 01/90081 describes amino alkyl lactam. WO 02/53564 describes novel quinuclidine derivatives. WO 02/00652 describes carbamates derived from arylalkyl amines. WO 02/06241 describes 1,2,3,5-tetrahydrobenzo(c) azepin-4-one derivatives.

A report in *J. Med. Chem.*, 44, p. 984 (2002), describes cyclohexylmethyl piperidinyl triphenylpropioamide derivatives as selective $M_3$ antagonist discriminating against the other receptor subtypes.

SUMMARY OF THE INVENTION

In one aspect, azabicyclo derivatives are provided as muscarinic receptor antagonists which can be useful as safe and effective therapeutic or prophylactic agents for the treatment of various diseases of the respiratory, urinary and gastrointestinal systems. Also provided are processes for the synthesis of such compounds.

In another aspect, pharmaceutical compositions containing such compounds are provided together with acceptable carriers, excipients or diluents which can be useful for the treatment of various diseases of the respiratory, urinary and gastrointestinal systems.

The disclosure also includes within its scope prodrugs of such compounds. In general, such prodrugs will be functionalized derivatives of these compounds which are readily converted in vivo into the defined compounds. Conventional procedures for the selection and preparation of suitable prodrugs are known to the artisan skilled in the art.

The enantiomers, diastereomers, N-oxides, polymorphs, pharmaceutically acceptable salts and pharmaceutically acceptable solvates of these compounds as well as metabolites having the same type of activity are also provided, as well as pharmaceutical compositions comprising such compounds, their prodrugs, metabolites, enantiomers, diastereomers, N-oxides, polymorphs, solvates or pharmaceutically acceptable salts thereof, in combination with a pharmaceutically acceptable carrier and optionally included excipients.

Other aspects will be set forth in the description which follows, and in part will be apparent from the description or may be learnt by the practice of the invention. The aspects may be realized and obtained by means of the mechanisms and combinations pointed out in the appended claims.

In accordance with one aspect, there are provided compounds having the structure of Formula I:

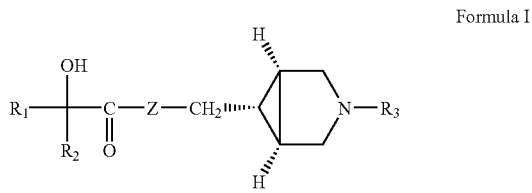

Formula I and their pharmaceutically acceptable salts, pharmaceutically acceptable solvates, esters, enantiomers, diastereomers, N-oxides, polymorphs, prodrugs, metabolites, wherein $R_1$ and $R_2$ are independently selected from $C_1$-$C_6$ alkyl, $C_3$-$C_7$ cycloalkyl, $C_3$-$C_7$ cycloalkenyl or optionally substituted phenyl wherein optional substituent(s) is/are selected from $C_1$-$C_3$ alkyl, $C_1$-$C_3$ alkoxy or halogen;

$R_3$ represents $C_1$-$C_6$ alkyl wherein 1-3 hydrogen atom(s) may be replaced by $C_5$-$C_7$ cycloalkyl, 1,3-dioxo-1,3-dihydroisoindolyl or optionally substituted phenyl wherein the optional substituent(s) is/are selected from $C_1$-$C_4$ alkyl or halogen;

Z represents oxygen or $NR_4$ wherein $R_4$ represents hydrogen or $C_1$-$C_3$ alkyl.

In accordance with a second aspect, there is provided a method for treatment or prophylaxis of an animal or a human suffering from a disease or disorder of the respiratory, urinary and gastrointestinal systems, wherein the disease or disorder is mediated through muscarinic receptors.

In accordance with a third aspect, there is provided a method for treatment or prophylaxis of an animal or a human suffering from a disease or disorder associated with muscarinic receptors, comprising administering to a patient in need thereof, an effective amount for muscarinic receptor antagonist compound as described above.

In accordance with a fourth aspect, there is provided a method for treatment or prophylaxis of an animal or a human suffering from a disease or disorder of the respiratory system such as bronchial asthma, chronic obstructive pulmonary disorders (COPD), pulmonary fibrosis, etc.; urinary system which induce such urinary disorders as urinary incontinence, lower urinary tract symptoms (LUTS), etc.; and gastrointestinal system such as irritable bowel syndrome, obesity, diabetes and gastrointestinal hyperkinesis with compounds as described above, wherein the disease or disorder is associated with muscarinic receptors.

In accordance with a fifth aspect, there are provided processes for preparing the compounds as described above.

Compounds described herein exhibit significant potency in terms of their activity, which was determined by in vitro receptor binding assays. The compounds are tested in vivo. Some of the compounds of the present invention were found to be potent muscarinic receptor antagonists with high affinity towards $M_3$ receptors. Therefore, pharmaceutical compositions for the possible treatment for diseases or disorders associated with muscarinic receptors are provided herein. In addition, such compounds can be administered orally or parenterally.

DETAILED DESCRIPTION OF THE INVENTION

The compounds described herein may be prepared by techniques well known in the art and familiar to the average synthetic organic chemist. In addition, these compounds may be prepared by the following reaction sequences as shown in Schemes I and II:

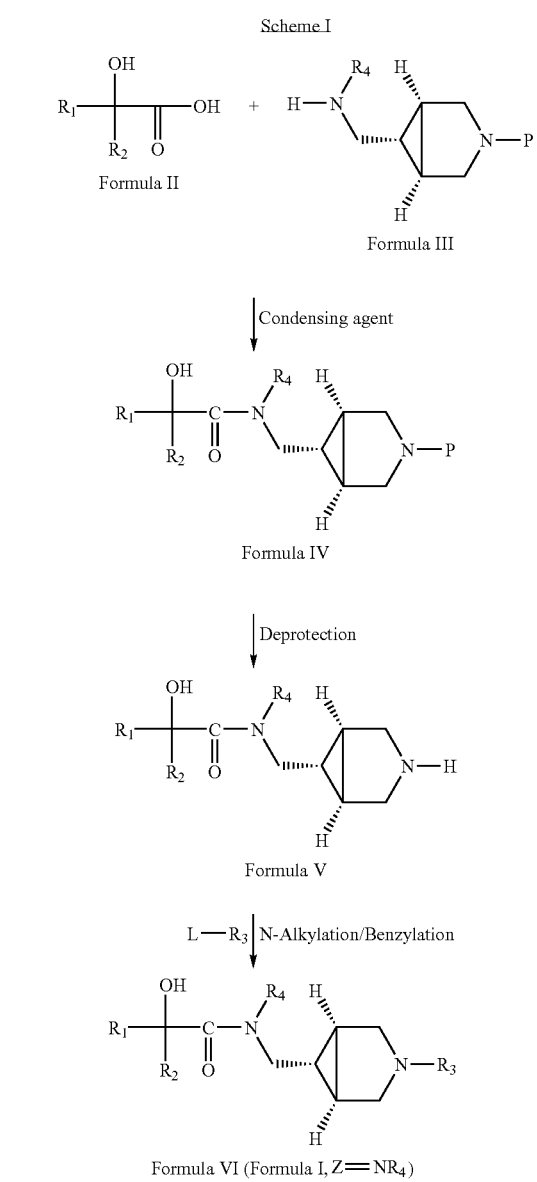

Compounds of Formula VI may be prepared by the illustrative reaction sequence of Scheme I, which depicts condensing a compound of Formula II with a compound of Formula III wherein $R_1$ and $R_2$ are independently selected from $C_1$-$C_6$ alkyl, $C_3$-$C_7$ cycloalkyl, $C_3$-$C_7$ cycloalkenyl or optionally substituted phenyl wherein optional substituent(s) is/are selected from $C_1$-$C_3$ alkyl, $C_1$-$C_3$ alkoxy or halogen; $R_4$ represents hydrogen or $C_1$-$C_3$ alkyl; P is any protecting group for an amino group, in the presence of N-methylmorpholine and 1-hydroxybenzotriazole and a condensing agent to give a protected compound of Formula IV, which on deprotection in the presence of a deprotecting agent in an organic solvent gives an unprotected intermediate of Formula V which is finally N-alkylated or benzylated with a suitable alkylating or benzylating agent L-R$_3$ to give a compound of Formula VI wherein L is any leaving group and R$_3$ represents C$_1$-C$_6$ alkyl wherein 1-3 hydrogen atom(s) may be replaced by C$_5$-C$_7$ cycloalkyl, 1,3-dioxo-1,3-dihydro-isoindolyl or optionally substituted phenyl wherein the optional substituent is/are selected from C$_1$-C$_4$ alkyl or halogen. P is any protecting group for an amino group for a compound of Formula III and is selected from benzyl and t-butyloxy carbonyl groups.

The reaction of a compound of Formula II with a compound of Formula III to give a compound of Formula IV can be carried out in the presence of a condensing agent, for example, 1-(3-dimethylaminopropyl)-3-ethyl carbodiimide hydrochloride (EDC), 1,8-diazabicyclo[5.4.0]undec-7-ene (DBU) or 1,3-dicyclohexylcarbodiimide (DCC).

The reaction of a compound of Formula II with a compound of Formula III to give a compound of Formula IV can be carried out in a solvent, for example, dimethylformamide, dimethylsulfoxide, benzene, toluene, xylene or chloroform, at a temperature ranging from about 0-140° C.

The deprotection of a compound of Formula IV to give a compound of Formula V can be carried out with a deprotecting agent, for example, palladium on carbon and hydrogen, ammonium formate and palladium on carbon, trifluoroacetic acid (TFA) or hydrochloric acid.

The deprotection of a compound of Formula IV to give a compound of Formula V can be carried out in an organic solvent, for example, methanol, ethanol, tetrahydrofuran or acetonitrile, at a temperature ranging from about 10-50° C.

The N-alkylation or benzylation of a compound of Formula V to give a compound of Formula VI can be carried out with an alkylating or benzylating agent, L-R$_3$ wherein L is any leaving group, known in the art, for example, halogen, O-mestyl or O-tosyl group.

The N-alkylation or benzylation of a compound of Formula V to give a compound of Formula VI can be carried out in an optional presence of potassium carbonate and potassium iodide in a suitable organic solvent, for example, dimethylformamide, dimethyl sulfoxide, tetrahydrofuran or acetonitrile, at a temperature ranging from about 25-100° C.

Scheme II

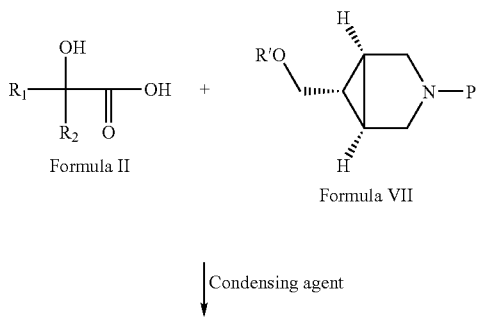

Formula II

Condensing agent

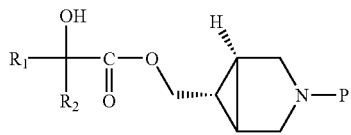

Formula VIII

Deprotection

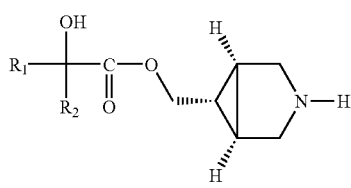

Formula IX

L—R$_3$ | N-Alkylation/Benzylation

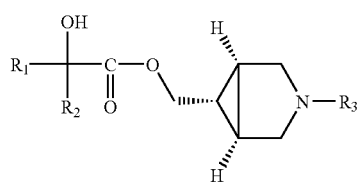

Formula X (Formula I, Z=O)

Compounds of Formula X may be prepared by the illustrative reaction sequences as shown in Scheme II, which depicts condensing a compound of Formula II with a compound of Formula VII wherein R$_1$ and R$_2$ are independently selected from C$_1$-C$_6$ alkyl, C$_3$-C$_7$ cycloalkyl, C$_3$-C$_7$ cycloalkenyl or optionally substituted phenyl wherein optional substituent(s) is/are selected C$_1$-C$_3$ alkyl, C$_1$-C$_3$ alkoxy or halogen;

P is any protecting group for an amino group, R' is any protecting group for a hydroxy group, in a condensing agent to give a compound of Formula VII which on deprotection in the presence of deprotecting agent in an organic solvent gives an unprotected intermediate of Formula IX which is finally alkylated or benzylated with suitable alkylating or benzylating agent L-R$_3$ to give a compound of Formula X wherein L is any leaving group and R$_3$ represents C$_1$-C$_6$ alkyl wherein 1-3 hydrogen atom(s) may be replaced by C$_5$-C$_7$ cycloalkyl, 1,3-dioxo-1,3-dihydro-isoindolyl or optionally substituted phenyl wherein the optional substituent is/are selected from C$_1$-C$_4$ alkyl or halogen.

P is any protecting group for an amino group for a compound of Formula VII and is selected from benzyl and t-butyloxy carbonyl groups.

R' is any protecting group for a hydroxy group for a compound of Formula VII and is selected from p-toluene sulfonyl and methane sulfonyl groups.

The reaction of a compound of Formula II with a compound of Formula VII to give a compound of Formula VIII can be carried out in the presence of a condensing agent, for example, 1,8-diazabicyclo[5.4.0]undecan-7-ene (DBU) or 1,4-diazabicyclo[2.2.2]octane (DABCO).

The reaction of a compound of Formula II with a compound of Formula VII to give a compound of Formula VIII can be carried out in a solvent, for example, benzene, toluene or xylene.

The deprotection of a compound of Formula VIII to give a compound of Formula IX can be carried out in the presence of a deprotecting agent, for example, palladium on carbon and hydrogen gas or ammonium formate and palladium on carbon.

The deprotection of a compound of Formula VIII to give a compound of Formula IX can be carried out in a solvent, for example, methanol or ethanol.

The N-alkylation or benzylation of a compound of Formula IX to give a compound of Formula X can be carried out with an alkylating or benzylating agent, L-R$_3$ wherein L is any leaving group, known in the art, for example, halogen, O-mestyl or O-tosyl group.

The alkylation or benzylation of a compound of Formula IX to give a compound of Formula X can be carried out with an alkylating or benzylating agent, L-R$_3$ in a solvent, for example, dimethylformamide, dimethylsulfoxide, tetrahydrofuran or acetonitrile, at temperatures ranging from about 25-100° C.

In the above scheme, where specific bases, condensing agents, protecting groups, deprotecting agents, N-alkylating/benzylating agents, solvents, catalysts etc. are mentioned, it is to be understood that other bases, condensing agents, protecting groups, deprotecting agents, N-alkylating/benzylating agents, solvents, catalysts etc. known to those skilled in the art may be used. Similarly, the reaction temperature and duration may be adjusted according to the desired needs.

Suitable salts of the compounds represented by the Formula I were prepared so as to solubilize the compound in aqueous medium for biological evaluations. Examples of such salts include pharmacologically acceptable salts such as inorganic acid salts (e.g., hydrochloride, hydrobromide, sulphate, nitrate and phosphorate), organic acid salts (e.g., acetate, tartarate, citrate, fumarate, maleate, tolounesulphonate and methanesulphonate). When carboxyl group is included in the Formula I as a substituent, it may be an alkali metal salt (e.g., sodium, potassium, calcium, magnesium, and the like). These salts may be prepared by the usual prior art techniques, such as treating the compound with an equivalent amount of inorganic or organic, acid or base in a suitable solvent.

Preferred compounds according to the invention and capable of being produced by Schemes I and II as shown in Table I include:

| Compound No. | Chemical Name |
|---|---|
| 1. | (2R, 2S) (1α, 5α, 6α)-N- {-[4-(1,3-dioxo-1,3-dihydro-isoindol-2-yl)-butyl]-3-azabicyclo[3.1.0]hex-6-yl-methyl}-2-hydroxy-2-cyclopentyl-2-phenylacetamide |
| 2. | (2R) (1α, 5α, 6α)-N-(3-Benzyl-3-azabicyclo[3.1.0]hex-6-yl-methyl)-2-hydroxy-2-cyclopent-1-enyl-2-phenylacetamide |
| 3. | (2R, 2S) (1α, 5α, 6α)-N-(3-Isopropyl-3-azabicyclo[3.1.0]hex-6-yl-methyl)-2-hydroxy-2-cyclopentyl-2-phenylacetamide |
| 4. | (2R, 2S) (1α, 5α, 6α)-N-(3-Diphenylmethyl-3-azabicyclo[3.1.0]hex-6-yl-methyl)-2-hydroxy-2-cyclopentyl-2-phenylacetamide |
| 5. | (2R, 2S) (1α, 5α, 6α)-N-(3-sec-butyl-3-azabicyclo[3.1.0]hex-6-yl-methyl)-2-hydroxy-2-cyclopentyl-2-phenylacetamide |
| 6. | (2R, 2S) (1α, 5α, 6α)-N-(3-Benzyl-3-azabicyclo[3.1.0]hex-6-yl-methyl)-2-hydroxy-2-(3-pentyl)-2-phenylacetamide |
| 7. | (2R, 2S) (1α, 5α, 6α)-N-(3-Benzyl-3-azabicyclo[3.1.0]hex-6-yl-methyl)-2-hydroxy-2-cyclohexyl-2-(4-methoxyphenyl) acetamide |
| 8. | (1α, 5α, 6α)-N-(3-Benzyl-3-azabicyclo[3.1.0]hex-6-yl-methyl)-2-hydroxy-2-phenyl-(N-ethyl)-2-phenylacetamide |
| 9. | (2R, 2S) (1α, 5α, 6α)-N-(3-Benzyl-3-azabicyclo[3.1.0]hex-6-yl-methyl)-2-hydroxy-2-cyclopentyl-(N-ethyl)-2-phenylacetamide |
| 10. | (2R, 2S) (1α, 5α, 6α)-N-(3-Benzyl-3-azabicyclo[3.1.0]hex-6-yl-methyl)-2-hydroxy-2-cyclohexyl-(N-ethyl)-2-phenylacetamide |
| 11. | (2R, 2S) (1α, 5α, 6α)-N-(3-Benzyl-3-azabicyclo[3.1.0]hex-6-yl-methyl)-2-hydroxy-2-(3-pentyl)-(N-methyl)-2-phenylacetamide |
| 12. | (2R, 2S) (1α, 5α, 6α)-N-(3-Benzyl-3-azabicyclo[3.1.0]hex-6-yl-methyl)-2-hydroxy-2-(sec-butyl)-(N-methyl)-2-phenylacetamide |
| 13. | (2R, 2S) (1α, 5α, 6α)-N-(3-Benzyl-3-azabicyclo[3.1.0]hex-6-yl-methyl)-2-hydroxy-2-isopropyl-(N-methyl)-2-phenylacetamide |
| 14. | (2R, 2S) (1α, 5α, 6α)-N-[3-(4-tert-butyl-benzyl)-3-azabicyclo[3.1.0]hex-6-yl-methyl]-2-hydroxy-2-cyclopentyl-2-phenylacetamide |
| 15. | (2R, 2S) (1α, 5α, 6α)-N-(3-Benzyl-3-azabicyclo[3.1.0]hex-6-yl-methyl)-2-hydroxy-2-cyclohex-2-enyl-2-phenylacetamide |
| 16. | (1α, 5α, 6α)-N-[3-(4-methylbenzyl)-3-azabicyclo[3.1.0]hex-6-yl-methyl]-2-hydroxy-2,2-diphenylacetamide |
| 17. | (2R, 2S) (1α, 5α, 6α)-N-[3-(4-methylbenzyl)-3-azabicyclo[3.1.0]hex-6-yl-methyl]-2-hydroxy-2-cyclopentyl-2-phenylacetamide |
| 18. | (2R, 2S) (1α, 5α, 6α)-N-[3-(4-methylbenzyl)-3-azabicyclo[3.1.0]hex-6-yl-methyl]-2-hydroxy-2-cyclohexyl-2-phenylacetamide |
| 19. | (1α, 5α, 6α)-N-[3-(3-methylbenzyl)-3-azabicyclo[3.1.0]hex-6-yl-methyl]-2-hydroxy-2,2-diphenylacetamide |
| 20. | (1α, 5α, 6α)-N-[3-(3-fluorobenzyl)-3-azabicyclo[3.1.0]hex-6-yl-methyl]-2-hydroxy-2,2-diphenylacetamide |
| 21. | (2R, 2S) (1α, 5α, 6α)-N-[3-(3-fluorobenzyl)-3-azabicyclo[3.1.0]hex-6-yl-methyl]-2-hydroxy-2-cyclohexyl-2-phenylacetamide |
| 22. | (2R, 2S) (1α, 5α, 6α)-N-[2-(2,4-difluorobenzyl)-3-azabicyclo[3.1.0]hex-6-yl-methyl]-2-hydroxy-2-cyclohexyl-2-phenylacetamide |
| 23. | (1α, 5α, 6α)-N-[3-(2,4-difluorobenzyl)-3-azabicyclo[3.1.0]hex-6-yl-methyl]-2-hydroxy-2,2-diphenylacetamide |
| 24. | (2R, 2S) (1α, 5α, 6α)-N-[3-(3-methylbenzyl)-3-azabicyclo[3.1.0]hex-6-yl-methyl]-2-hydroxy-2-cyclopentyl-2-phenylacetamide |
| 25. | (2R, 2S) (1α, 5α, 6α)-N-(3-benzyl-3-azabicyclo[3.1.0]hex-6-yl-methyl)-2-hydroxy-2-(4-methylphenyl)-2-phenylacetamide |
| 26. | (2R, 2S) (1α, 5α, 6α)-N-(3-benzyl-3-azabicyclo[3.1.0]hex-6-yl-methyl)-2-hydroxy-2-(4-methylphenyl)-(N-methyl)-2-phenylacetamide |
| 27. | (2R, 2S) (1α, 5α, 6α)-N-(3-benzyl-3-azabicyclo[3.1.0]hex-6-yl-methyl)-2-hydroxy-2-(4-fluorophenyl)-2-phenylacetamide |
| 28. | (2R, 2S) (1α, 5α, 6α)-(3-benzyl-3-azabicyclo[3.1.0]hex-6-yl-methyl)-2-hydroxy-2-(4-fluorophenyl)-2-phenyl acetic acid ester |
| 29. | (2R, 2S) (1α, 5α, 6α)-N-(3-benzyl-3-azabicyclo[3.1.0]hex-6-yl-methyl)-2-hydroxy-2-(4-fluorophenyl)-(N-methyl)-2-phenylacetamide |
| 30. | (2R, 2S) (1α, 5α, 6α)-N-(3-benzyl-3-azabicyclo[3.1.0]hex-6-yl-methyl)-2-hydroxy-2-(3-methylphenyl)-2-phenylacetamide |
| 31. | (2R, 2S) (1α, 5α, 6α)-N-(3-benzyl-3-azabicyclo[3.1.0]hex-6-yl-methyl)-2-hydroxy-2-(3-methylphenyl)-(N-methyl)-2-phenylacetamide |
| 32. | (2R, 2S) (1α, 5α, 6α)-(3-benzyl-3-azabicyclo[3.1.0]hex-6-yl-methyl)-2-hydroxy-2-(3-methylphenyl)-2-phenyl acetic acid ester |
| 33. | (2R, 2S) (1α, 5α, 6α)-(3-benzyl-3-azabicyclo[3.1.0]hex-6-yl-methyl)-2-hydroxy-2-cyclopentyl-2-(3-methylphenyl) acetic acid ester |
| 34. | (2R, 2S) (1α, 5α, 6α)-(3-benzyl-3-azabicyclo[3.1.0]hex-6-yl-methyl)-2-hydroxy-2-cyclopentyl-2-(3-methylphenyl) acetic acid ester tartarate salt |
| 35. | (2R, 2S) (1α, 5α, 6α)-N-(3-benzyl-3-azabicyclo[3.1.0]hex-6-yl-methyl)-2-hydroxy-2-cyclopentyl-2-(3-methylphenyl) acetamide |
| 36. | (2R, 2S) (1α, 5α, 6α)-N-(3-benzyl-3-azabicyclo[3.1.0]hex-6-yl-methyl)-2-hydroxy-2-cyclopentyl-2-(3-methylphenyl) acetamide tartarate salt |
| 37. | (1α, 5α, 6α)-N-(3-benzyl-3-azabicyclo[3.1.0]hex-6-yl-methyl)-2-hydroxy-2,2-di(4-fluorophenyl)acetic acid ester |

-continued

| Compound No. | Chemical Name |
|---|---|
| 38. | (1α, 5α, 6α)-N-(3-benzyl-3-azabicyclo[3.1.0]hex-6-yl-methyl]-2-hydroxy-2,2-di(4-fluorophenyl)-acetamide |
| 39. | (2R, 2S) (1α, 5α, 6α)-(3-benzyl-3-azabicyclo[3.1.0]hex-6-yl-methyl]-2-hydroxy-2-cyclobutyl-2-phenyl acetic acid ester |
| 40. | (2R, 2S) (1α, 5α, 6α)-N-(3-cyclohexylmethyl-3-azabicyclo[3.1.0]hex-6-yl-methyl)-2-hydroxy-2-cyclopentyl-2-phenylacetamide |
| 41. | (2R) (1α, 5α, 6α)-N-(3-benzyl-3-azabicyclo[3.1.0]hex-6-yl-methyl)-2-hydroxy-2-cyclopentyl-(N-methyl)-2-phenylacetamide |
| 42. | (2R, 2S) (1α, 5α, 6α)-N-(3-benzyl-3-azabicyclo[3.1.0]hex-6-yl-methyl]-2-hydroxy-2-cyclopentyl-2-(4-methylphenyl) acetamide |
| 43. | (2R, 2S) (1α, 5α, 6α)-(3-benzyl-3-azabicyclo[3.1.0]hex-6-yl-methyl)-2-hydroxy-2-phenyl-2-(4-methylphenyl) acetic acid ester |
| 44. | (2R, 2S) (1α, 5α, 6α)-(3-benzyl-3-azabicyclo[3.1.0]hex-6-yl-methyl)-2-hydroxy-2-methyl-2-phenyl acetic acid ester |
| 45. | (2R, 2S) (1α, 5α, 6α)-N-(3-benzyl-3-azabicyclo[3.1.0]hex-6-yl-methyl]-2-hydroxy-2-methyl-2-phenyl acetamide |
| 46. | (2R, 2S) (1α, 5α, 6α)-(3-benzyl-3-azabicyclo[3.1.0]hex-6-yl-methyl)-2-hydroxy-2-isopropyl-2-phenyl acetic acid ester |
| 47. | (1α, 5α, 6α)-N-(3-methyl-3-azabicyclo[3.1.0]hex-6-yl-methyl)-2-hydroxy-2-phenyl-(N-methyl)-2-phenylacetamide |
| 48. | (2R, 2S) (1α, 5α, 6α)-N-(3-benzyl-3-azabicyclo[3.1.0]hex-6-yl-methyl]-2-hydroxy-2-(3-methylphenyl)-2-(3-methylphenyl) acetamide |
| 49. | (2R, 2S) (1α, 5α, 6α)-(3-benzyl-3-azabicyclo[3.1.0]hex-6-yl-methyl)-2-hydroxy-2-(3-pentyl)-2-phenyl acetic acid ester |
| 50. | (2R, 2S) (1α, 5α, 6α)-N-(3-benzyl-3-azabicyclo[3.1.0]hex-6-yl-methyl)-2-hydroxy-2-methyl-(N-methyl)-2-phenylacetamide |

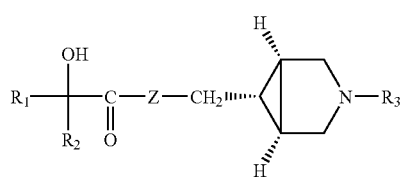

Formula I

TABLE 1

| Compound No. | $R_1$ | $R_2$ | $R_3$ | Z |
|---|---|---|---|---|
| 1 | Phenyl | Cyclopentyl | 1,3-dioxo-1,3-dihydro-isoindol-2-yl)-butyl | NH |
| 2 | Phenyl | Cyclopent-1-enyl | Benzyl | NH |
| 3 | Phenyl | Cyclopentyl | Isopropyl | NH |
| 4 | Phenyl | Cyclopentyl | Diphenylmethyl | NH |
| 5 | Phenyl | Cyclopentyl | Sec-butyl | NH |
| 6 | Phenyl | 3-pentyl | Benzyl | NH |
| 7 | 4-methoxyphenyl | Cyclohexyl | Benzyl | NH |
| 8 | Phenyl | Phenyl | Benzyl | NEt |
| 9 | Phenyl | Cyclopentyl | Benzyl | NEt |
| 10 | Phenyl | Cyclohexyl | Benzyl | NEt |
| 11 | Phenyl | 3-pentyl | Benzyl | NMe |
| 12 | Phenyl | Sec-butyl | Benzyl | NMe |
| 13 | Phenyl | Isopropyl | Benzyl | NMe |
| 14 | Phenyl | Cyclopentyl | 4-tert-butylbenzyl | NH |
| 15 | Phenyl | Cyclohex-2-enyl | Benzyl | NH |
| 16 | Phenyl | Phenyl | 4-methylbenzyl | NH |
| 17 | Phenyl | Cyclopentyl | 4-methylbenzyl | NH |
| 18 | Phenyl | Cyclohexyl | 4-methylbenzyl | NH |
| 19 | Phenyl | Phenyl | 3-methylbenzyl | NH |
| 20 | Phenyl | Phenyl | 3-fluorobenzyl | NH |
| 21 | Phenyl | Cyclohexyl | 3-fluorobenzyl | NH |
| 22 | Phenyl | Cyclohexyl | 2,4-difluorobenzyl | NH |
| 23 | Phenyl | Phenyl | 2,4-difluorobenzyl | NH |
| 24 | Phenyl | Cyclopentyl | 3-methylbenzyl | NH |
| 25 | Phenyl | 4-methylphenyl | Benzyl | NH |
| 26 | Phenyl | 4-methylphenyl | Benzyl | NMe |
| 27 | Phenyl | 4-fluorophenyl | Benzyl | NH |
| 28 | Phenyl | 4-fluorophenyl | Benzyl | O |
| 29 | Phenyl | 4-fluorophenyl | Benzyl | NMe |
| 30 | Phenyl | 3-methylphenyl | Benzyl | NH |
| 31 | Phenyl | 3-methylphenyl | Benzyl | NMe |
| 32 | Phenyl | 3-methylphenyl | Benzyl | O |
| 33 | 3-methylphenyl | Cyclopentyl | Benzyl | O |
| 34 (tartarate salt) | 3-methylphenyl | Cyclopentyl | Benzyl | O |
| 35 | 3-methylphenyl | Cyclopentyl | Benzyl | NH |
| 36 (tartarate salt) | 3-methylphenyl | Cyclopentyl | Benzyl | NH |
| 37 | 4-fluorophenyl | 4-fluorophenyl | Benzyl | O |
| 38 | 4-fluorophenyl | 4-fluorophenyl | Benzyl | NH |
| 39 | Phenyl | Cyclobutyl | Benzyl | O |
| 40 | Phenyl | Cyclopentyl | cyclohexylmethyl | NH |
| 41 | Phenyl | Cyclopentyl | Benzyl | NMe |
| 42 | 4-methylphenyl | Cyclopentyl | Benzyl | NH |
| 43 | 4-methylphenyl | phenyl | Benzyl | O |
| 44 | Phenyl | Methyl | Benzyl | O |
| 45 | Phenyl | Methyl | Benzyl | NH |
| 46 | Phenyl | Isopropyl | Benzyl | O |
| 47 | Phenyl | Phenyl | methyl | NMe |
| 48 | 3-methylphenyl | 3-methylphenyl | Benzyl | NH |
| 49 | Phenyl | 3-pentyl | Benzyl | O |
| 50 | Phenyl | Methyl | Benzyl | NMe |

Because of their valuable pharmacological properties, compounds disclosed herein may be administered to an animal for treatment orally, or by parenteral route. The pharmaceutical compositions containing such compounds are preferably produced and administered in dosage units, each unit containing a certain amount of at least one compound described herein and/or at least one physiologically acceptable addition salt thereof. The dosage may be varied over extremely wide limits as the compounds are effective at low dosage levels and relatively free of toxicity. The compounds may be administered in the low micromolar concentration, which is therapeutically effective, and the dosage may be increased as desired up to the maximum dosage tolerated by the patient.

Prodrugs of the compounds of Formula I are also provided. In general, such prodrugs will be functional derivatives of these compounds, which readily are converted in vivo into the defined compounds. Conventional procedures for the selection and preparation of suitable prodrugs are known.

Enantiomers, diastereomers, N-Oxides, polymorphs, solvates and pharmaceutically acceptable salts of these compounds as well as metabolites having the same type of activity are also provided, along with pharmaceutical compositions comprising the molecules of Formula I or pro drugs, metabolites, enantiomers, diastereomers, N-oxides, polymorphs, solvates or pharmaceutically acceptable salts thereof, in combination with pharmaceutically acceptable carriers and optionally included excipients.

The examples mentioned below demonstrate general synthetic procedures, as well as specific preparations of particular compounds. The examples are provided to illustrate the details of the invention and should not be constrained to limit the scope of the present invention.

Experimental Details

Various solvents, such as acetone, methanol, pyridine, ether, tetrahydrofuran, hexanes, and dichloromethane, were dried using various drying reagents according to the procedure described in the literature. IR spectra were recorded as nujol mulls or a thin neat film on a Perkin Elmer Paragon instrument, Nuclear Magnetic Resonance (NMR) were recorded on a Varian XL-300 MHz instrument using tetramethylsilane as an internal standard.

EXAMPLE 1

Preparation of (2R,2S)(1α,5α,6α)-N-(3-Benzyl-3-azabicyclo[3.1.0]hex-6-yl-methyl)-2-hydroxy-2-cyclohexyl-2-(4-methoxyphenyl)acetamide (Compound No. 7)

Step a: Preparation of (3-benzyl-3-azabicyclo[3.1.0]hex-6-yl)-methylamine

This compound was prepared following procedures described in EP 0413455.

Step b: Preparation of (2R,2S)(1α,5α,6α)-N-(3-Benzyl-3-azabicyclo[3.1.0]hex-6-yl-methyl)-2-hydroxy-2-cyclohexyl-2-(4-methoxyphenyl)acetamide A solution of cyclohexyl-hydroxy-phenyl acetic acid (prepared following the procedure described in *J. Amer. Chem. Soc.*, 1953; 75: 2654 and *J. Org. Chem.*, (2000), 65:6283) (1.13 mmole) and (3-benzyl-3-azabicyclo[3.1.0]hex-6-yl)-methylamine (1.25 mmole) in dimethylformamide cooled in an ice bath and 1-hydroxybenzotriazole (1.25 mmole), and N-methylmorpholine (2.26 mmole) were added. The reaction mixture was stirred for 1 hour in ice bath and then 1-(3-dimethylaminopropyl)-3-ethylcarbodiimide hydrochloride (1.189 mmole) was added. The reaction mixture was stirred in ice bath for about 2 hours and then at room temperature overnight. The reaction mixture was poured into saturated bicarbonate solution and extracted with ethyl acetate. The organic layer was washed with water, dried and concentrated under reduced pressure. The residue was purified by column chromatography, eluting the compound with 40% ethyl acetate-hexane.

m. pt: 140-144° (white solid) IR (DCM): 3395.2, 2931.9, 1644.9 cm$^{-1}$ H$^1$-NMR (CDCl$_3$, 300 MHz) δ-values: 7.50 (7H, d, 9 Hz), 7.26 (3H, bs), 6.87 (2H, d, 9 Hz), 6.62 (1H, bs), 3.78 (3H, s), 3.57 (2H, s), 3.10-2.91 (5H, m), 2.33 (3H, bs), 1.68-0.91 (14H, m) Mass: m/z 449.5 (M+1, 100%)

Similarly, the following compounds were prepared analogously, following the procedure described above with the appropriate substituions of reagents:

(2R,2S)(1α,5α,6α)-N-(3-benzyl-3-azabicyclo[3.1.0]hex-6-yl-methyl]-2-hydroxy-2-methyl-2-phenyl acetamide (Compound No. 45)

IR (DCM): 1653.6 cm$^{-1}$ H$^1$-NMR (CDCl$_3$, 300 MHz) δ-values: 7.53-7.56 (2H, m), 7.23-7.37 (8H, m), 6.50 (1H, brs), 3.56 (2H, s), 3.03-3.09 (2H, m), 2.90-2.93 (2H, m), 2.30-2.33 (2H, m), 1.80 (3H, s), 1.35-1.39 (m, 1H), 1.23-1.28 (m, 2H) Mass: m/z 351 (M+1)

(2R,2S)(1α,5α,6α)-N-(3-benzyl-3-azabicyclo[3.1.0]hex-6-yl-methyl)-2-hydroxy-2-(4-methylphenyl)-2-phenylacetamide (Compound No. 25)

H$^1$-NMR (CDCl$_3$, 300 MHz) δ-values: 7.45-7.23 (14H, m), 6.34 (1H, brs), 3.58-3.56 (2H, m), 3.18-3.13 (2H, m), 2.95-2.92 (2H, m), 2.34-2.22 (5H, m), 1.48-1.46 (3H, m) Mass: m/z 427.41 (M+1)

(2R,2S)(1α,5α,6α)-N-(3-benzyl-3-azabicyclo[3.1.0]hex-6-yl-methyl)-2-hydroxy-2-(4-fluorophenyl)-2-phenylacetamide (Compound No. 27)

H$^1$-NMR (CDCl$_3$, 300 MHz) δ-values: 7.44-7.12 (14H, m), 6.43 (1H, brs), 3.59 (1H, brs), 3.18-3.14 (2H, m), 2.97-2.94 (4H, m), 2.37-2.35 (2H, m), 1.47-1.30 (3H, m) Mass: m/z 431.49 (M+1)

(2R,2S)(1α,5α,6α)-N-(3-benzyl-3-azabicyclo[3.1.0]hex-6-yl-methyl)-2-hydroxy-2-(3-methylphenyl)-2-phenylacetamide (Compound No. 30)

H$^1$-NMR (CDCl$_3$, 300 MHz) δ-values: 7.44-7.11 (14H, m), 6.38 (1H, brs), 3.61 (1H, m), 3.18-1.14 (2H, m), 2.99-2.96 (4H, m), 2.39-2.31 (5H, m), 1.31-1.28 (3H, m) Mass: 427.46 (M+1)

(2R)(1α,5α,6α)-N-(3-Benzyl-3-azabicyclo[3.1.0]hex-6-yl-methyl)-2-hydroxy-2-cyclopent-1-enyl-2-phenylacetamide (Compound No. 2)

IR (DCM): 1659.8 cm$^{-1}$ $^1$H-NMR (CDCl$_3$) δ-values: 7.48-7.51 (m, 2H), 7.27-7.37 (m, 8H), 6.23 (brs, 1H), 5.67 (s, 1H), 3.63 (s, 2H), 2.97-3.18 (m, 6H), 2.37-2.42 (m, 2H), 1.88-2.08 (m, 4H), 1.23-1.31 (m, 3H)

(2R,2S)(1α,5α,6α)-N-(3-Benzyl-3-azabicyclo[3.1.0]hex-6-yl-methyl)-2-hydroxy-2-(3-pentyl)-2-phenylacetamide (Compound No. 6)

m.p: 100-104° C. IR (KBr): 1659.3 cm$^{-1}$ $^1$H-NMR (CDCl$_3$) δ-values: 7.61-7.63 (m, 2H), 7.22-7.35 (m, 8H), 6.66 (brs, 1H), 3.56 (s, 2H), 2.88-3.07 (m, 4H), 2.81 (s, 1H), 2.29-2.33 (m, 3H), 1.20-1.41 (m, 7H), 0.99-1.04 (t, 3H, J=9 Hz), 0.77-0.82 (t, 3H, J=9 Hz) Mass: 407 (M+1)

(1α,5α,6α)-N-(3-benzyl-3-azabicyclo[3.1.0]hex-6-yl-methyl]-2-hydroxy-2,2-di(4-fluorophenyl)acetamide (Compound No. 38)

IR (DCM): 3408.9, 1665 cm$^{-1}$ $^1$H-NMR (CDCl$_3$, 300 MHz) δ-values: 7.41-6.78 (13H, m), 6.44 (1H, bs), 4.00 (1H, bs), 3.57 (2H, s), 3.15 (2H, m), 2.93 (2H, m), 2.33 (2H, m), 1.47-1.25 (3H, m) Mass: m/z 449.2 (M+1)

(2R,2S)(1α,5α,6α)-N-(3-benzyl-3-azabicyclo[3.1.0]hex-6-yl-methyl]-2-hydroxy-2-cyclopentyl-2-(4-methylphenyl)acetamide (Compound No. 42)

$H^1$-NMR (CDCl$_3$) δ-values: 7.48-7.45 (2H, m), 7.29-7.12 (7H, m), 6.46 (1H, brs), 3.56 (2H, s), 3.17 (1H, s), 3.04-2.97 (5H, m), 2.92-2.89 (5H, m), 1.36-1.28 (11H, m) Mass: 419.48 (M+1)

(1α,5α,6α)-N-(3-benzyl-3-azabicyclo[3.1.0]hex-6-yl-methyl]-2-hydroxy-2,2-di(3-methylphenyl)acetamide (Compound No. 48)

IR: 3403.1, 1658.8 cm$^{-1}$ $^1$H-NMR (CDCl$_3$, 300 MHz) δ-values: 7.32-7.11 (13H, m), 6.32 (1H, bs, NH), 4.0 (1H, bs), 3.57 (2H, s), 3.16 (2H, t, 6 Hz), 2.93 (2H, m), 2.32 (8H, s), 1.27 (3H, m) Mass: m/z 441.35 [100%] (M+1)

(2R,2S)(1α,5α,6α)-N-(3-Benzyl-3-azabicyclo[3.1.0]hex-6-yl-methyl)-2-hydroxy-2-cyclohex-2-enyl-2-phenylacetamide (Compound No. 15)

IR: 3407, 1652.3 cm$^{-1}$ H$^1$-NMR (CDCl$_3$, 300 MHz) δ-values: 7.61 (2H, d, 7.5 Hz), 7.37-7.22 (8H, m), 6.54 (1H, bs, NH), 5.67 (2H, m), 3.55 (2H, s), 3.15-2.98 (2H, m), 2.90 (2H, m), 2.7 (1H, bs), 2.30 (2H, m), 2.16-2.04 (3H, m), 1.70 (2H, bs), 1.48-1.34 (2H, m), 1.24 (2H, m) Mass: 417.6 (M+1)

(2R,2S)(1α,5α,6α)-N-(3-benzyl-3-azabicyclo[3.1.0]hex-6-yl-methyl)-2-hydroxy-2-cyclopentyl-2-(3-methylphenyl)acetamide (Compound No. 35)

EXAMPLE 2

Preparation of (1α,5α,6α)-N-(3-Benzyl-3-azabicyclo[3.1.0]hex-6-yl-methyl)-2-hydroxy-2-phenyl-(N-ethyl)-2-phenylacetamide (Compound No. 8)

Step a: Preparation of (3-benzyl-3-azabicyclo[3.1.0]hex-6-ylmethyl)-ethylamine

To a solution of mesylate in ethanol, ethylamine solution was added in a steel bomb which was tightened and placed in an oil bath at about 80° C. overnight. It was cooled down to −78° C. and was opened up. The content was evaporated. It was diluted with hydrochloride and ethyl acetate. Organic layer was separated. Aqueous layer was basified with 10% aqueous sodium hydroxide solution and extracted with dichloromethane. The dichloromethane layer was dried and evaporated to get the required product.

Step b: Preparation of (1α,5α,6α)-N-(3-Benzyl-3-azabicyclo[3.1.0]hex-6-yl-methyl)-2-hydroxy-2-phenyl-(N-ethyl)-2-phenylacetamide To a cold solution of benzillic acid (2.2 mmole, commercially available) and (3-benzyl-3-azabicyclo[3.1.0]hex-6-yl-methyl)-ethylamine (2.2 mmole) in dimethylformamide, N-methylmorpholine (4.4 mmole) and 1-hydroxybenzotriazole (2.2 mmole) were added at 0° C. and the mixture was stirred at 0° C. for about 1 hour. After 1 hour 1-(3-dimethylaminopropyl)-3-ethylcarbodiimide hydrochloride (2.2 mmole) was added to it. The reaction mixture was then stirred at same temperature for about 20 mins and then at room temperature overnight. Reaction mixture was quenched by addition of water and the organic layer extracted with ethyl acetate. The organic layer was washed with water, brine, dried over anhydrous sodium sulphate and then concentrated to get crude compound. Purification was done by column chromatography using 20% ethyl acetate-hexane as eluent.

IR: 3315.9, 1628 cm$^{-1}$ H$^1$-NMR (CDCl$_3$, 300 MHz) δ-values: 7.40-7.15 (15H, bm), 6.25 (1H, bs), 3.61 (2H, s), 3.43-3.36 (2H, m), 3.14 (1H, bd, 6 Hz), 2.99 (1H, d, 6 Hz), 2.86 (1H, bs), 2.63 (1H, bs), 2.37 (1H, bs), 2.71 (1H, bs), 1.47 (1H, bs), 1.25 (3H, bs), 0.77 (1H, bs) Mass: m/z 441.8 (M+1)

Similarly, the following compounds were prepared analogously, following the above procedure with appropriate substitutions of reagents:

(2R,2S)(1α,5α,6α)-N-(3-Benzyl-3-azabicyclo[3.1.0]hex-6-yl-methyl)-2-hydroxy-2-cyclopentyl-(N-ethyl)-2-phenylacetamide (Compound No. 9)

IR: 3408.1, 1619.8 cm$^{-1}$ H$^1$-NMR (CDCl$_3$, 300 MHz) δ-values: 7.42-7.2 (10H, m), 5.55 (1H, bs, OH), 3.5-3.51 (3H, bs), 3.21 (2H, m), 2.89 (4H, bs), 2.28 (2H, bs), 1.84 (2H, m), 1.73-1.45 (5H, m), 1.30 (3H, bs), 1.08 (3H, t, 6 Hz), 0.88 (2H, m) Mass: m/z 433.4 (M+1)

(2R,2S)(1α,5α,6α)-N-(3-Benzyl-3-azabicyclo[3.1.0]hex-6-yl-methyl)-2-hydroxy-2-cyclohexyl-(N-ethyl)-2-phenylacetamide (Compound No. 10)

m.pt: 101.4-1.5° C. IR: 3299, 1613.2 cm$^{-1}$ H$^1$-NMR (CDCl$_3$, 300 MHz) δ-values: 7.41-7.17 (10H, m), 5.38 (1H, bs), 3.53 (2H, bs), 3.29 (4H, m), 2.84 (4H, m), 1.51-1.20 (12H, m), 1.08 (3H, t, 6 Hz), 0.88 (2H, m) Mass: m/z 447.4

(2R,2S)(1α,5α,6α)-N-(3-benzyl-3-azabicyclo[3.1.0]hex-6-yl-methyl)-2-hydroxy-2-(4-methylphenyl)-(N-methyl)-2-phenylacetamide (Compound No. 26)

IR: 1630.6 cm$^{-1}$ H$^1$-NMR (CDCl$_3$, 300 MHz) δ-values: 7.40-7.14 (14H, m), 3.59-3.32 (4H, m), 3.12-2.34 (11H, m), 1.33-1.30 (3H, m) Mass: 441.43 (M+1)

(2R,2S)(1α,5α,6α)-N-(3-benzyl-3-azabicyclo[3.1.0]hex-6-yl-methyl)-2-hydroxy-2-(4-fluorophenyl)-(N-methyl)-2-phenylacetamide (Compound No. 29)

H$^1$-NMR (CDCl$_3$, 300 MHz) δ-values: 7.35-7.02 (14H, m), 3.60-2.35 (11H, m), 1.32-1.30 (3H, m) Mass: 445.40 (M+1)

(2R,2S)(1α,5α,6α)-N-(3-benzyl-3-azabicyclo[3.1.0]hex-6-yl-methyl)-2-hydroxy-2-(3-methylphenyl)-(N-methyl)-2-phenylacetamide (Compound No. 31)

H$^1$-NMR (CDCl$_3$, 300 MHz) δ-values: 7.38-7.11 (14H, m), 3.44-2.00 (14H, m), 1.31-1.28 (3H, m) Mass: 441.56 (M+1)

(2R,2S)(1α,5α,6α)-N-(3-Benzyl-3-azabicyclo[3.1.0]hex-6-yl-methyl)-2-hydroxy-2-(3-pentyl)-(N-methyl)-2-phenylacetamide (Compound No. 11)

IR (DCM): 1621.4 cm$^{-1}$ $^1$H-NMR (CDCl$_3$) δ-values: 7.21-7.40 (m, 10H), 3.35-3.53 (m, 3H), 2.75-2.81 (m, 5H), 2.26 (m, 2H), 1.33-1.66 (m, 6H), 0.88-1.02 (m, 9H) Mass: 421 (M+1)

(2R,2S)(1α,5α,6α)-N-(3-Benzyl-3-azabicyclo[3.1.0]
hex-6-yl-methyl)-2-hydroxy-2-(sec-butyl)-(N-methyl)-2-phenylacetamide (Compound No. 12)

IR (DCM): 1621.7 cm$^{-1}$ $^1$H-NMR (CDCl$_3$) δ-values: 7.23-7.43 (m, 10H), 5.05 (brs, 1H), 3.53 (s, 2H), 2.52-2.83 (m, 5H), 2.25-2.28 (m, 2H), 1.58-1.70 (m, 3H), 0.83-1.00 (m, 11H) Mass: 407 (M+1)

(2R,2S)(1α,5α,6α)-N-(3-Benzyl-3-azabicyclo[3.1.0]
hex-6-yl-methyl)-2-hydroxy-2-isopropyl-(N-methyl)-2-phenylacetamide (Compound No. 13)

IR (DCM): 1622.5 cm$^{-1}$ $^1$H-NMR (CDCl$_3$) δ-values: 7.22-7.44 (m, 10H), 5.21 (brs, 1H), 3.34-3.53 (m, 3H), 2.78-2.99 (m, 5H), 2.25 (m, 2H), 1.57 (m, 2H), 0.71-1.06 (m, 9H) Mass: 393 (M+1)

(2R)(1α,5α,6α)-N-(3-benzyl-3-azabicyclo[3.1.0]
hex-6-yl-methyl)-2-hydroxy-2-cyclopentyl-(N-methyl)-2-phenylacetamide (Compound No. 41)

IR (DCM): 1623.9 cm$^{-1}$ $^1$H-NMR (CDCl$_3$, 300 MHz) δ-values: 7.39-7.42 (2H, m), 7.23-7.33 (8H, m), 3.54 (2H, s), 2.76-2.96 (7H, m), 2.28 (2H, brs), 1.30-1.85 (9H, m), 0.88 (3H, brs) Mass: m/z 419 (M+1)

(2R,2S)(1α,5α,6α)-N-(3-benzyl-3-azabicyclo[3.1.0]
hex-6-yl-methyl)-2-hydroxy-2-methyl-(N-methyl)-2-phenylacetamide (Compound No. 50)

IR (DCM): 1723.9 cm$^{-1}$ $^1$H-NMR (CDCl$_3$) δ-values: 7.14-7.58 (m, 10H), 3.72 (m, 2H), 3.17-3.24 (m, 2H), 2.96 (s, 3H), 2.88 (s, 3H), 2.49-2.63 (m, 2H), 1.77-1.95 (m, 2H), 1.46 (m, 1H), 0.88-0.98 (m, 2H) Mass: 365 (M+1)

EXAMPLE 3

Preparation of (2R,2S)(1α,5α,6α)-(3-benzyl-3-azabicyclo[3.1.0]hex-6-yl-methyl]-2-hydroxy-2-cyclobutyl-2-phenyl acetic acid ester
(Compound No. 39)

Method for the Preparation of
3-benzyl-6-bromomethyl-3-azabicyclo[3.1.0]hexane

To a solution of 3-benzyl-3-azabicyclo[3.1.0]hex-6-yl methanol (Synlett, 1996, 1097-99) (0.203 gm, 1 mmol) in carbon tetrachloride, phosphorous bromide (0.04 ml, 0.05 mmol) was added dropwise at room temperature. Reaction mixture was refluxed for about 5 hours (during refluxing a white precipitate appeared which turned to sticky yellow) then stirred at room temperature for overnight. Reaction mixture was quenched with water. Organic layer was separated. The sticky material was stirred in excess of chloroform. The combined organic layer was washed with 10% aqueous solution of sodium hydroxide, water and brine, dried over anhydrous sodium sulphate and concentrated under reduced pressure.

To a solution of 2-cyclobutyl-2-hydroxy-2-phenyl acetic acid (prepared following the procedures described in *J. Amer. Chem. Soc.*, 75, 2654 (1953) and *J. Org. Chem.*, 65, 6283 (2000); 0.932 mmole) and 3-benzyl-6-bromomethyl-3-azabicyclo[3.1.0]hexane (as prepared above; 0.932 mmole) in benzene,1,8-diazabicyclo[5.4.0]undecane-7-ene (1.11 mmole) was added and the mixture was refluxed for about 4 hours and then cooled to room temperature and stirred for overnight. The reaction mixture was quenched by addition of water, and extracted with ethyl acetate. The organic layer was washed with water, then brine, and dried over anhydrous sodium sulphate. The organic layer was evaporated to obtain the crude product, which was purified by column chromatography.

$^1$H-NMR (CDCl$_3$, 300 MHz) δ-values: 7.57 (2H, d, 7 Hz), 7.32-7.21 (8H, m), 4.05-3.92 (2H, m), 3.79 (1H, s), 3.57 (2H, s), 3.31 (1H, m), 2.91 (2H, m), 2.32 (1H, 9 Hz), 2.09-2.0 (2H, m), 1.86-1.77 (4H, m), 1.61-7.56 (2H, m), 1.29 (2H, m)

Similarly, the following compounds were prepared analogously, following the above procedure with appropriate substitutions of reagents:

(2R,2S)(1α,5α,6α)-(3-benzyl-3-azabicyclo[3.1.0]
hex-6-yl-methyl)-2-hydroxy-2-(4-fluorophenyl)-2-phenyl acetic acid ester (Compound No. 28)

IR (DCM): 1726.2 cm$^{-1}$ H$^1$-NMR (CDCl$_3$, 300 MHz) δ-values: 7.45-6.96 (14H, m), 4.25 (1H, s), 4.12-4.09 (2H, m), 3.58-3.56 (2H, m), 2.93-2.90 (2H, m), 2.32-2.30 (2H, m), 1.31-1.25 (3H, m) Mass: 432.41 (+1)

(2R,2S)(1α,5α,6α)-(3-benzyl-3-azabicyclo[3.1.0]
hex-6-yl-methyl)-2-hydroxy-2-(3-methylphenyl)-2-phenyl acetic acid ester (Compound No. 32)

H$^1$-NMR (CDCl$_3$, 300 MHz) δ-values: 7.46-7.09 (14H, m), 4.23-4.21 (1H, m), 4.11-4.08 (2H, m), 3.56-3.47 (2H, m), 2.92-2.89 (2H, m), 2.32-2.30 (5H, m), 1.30-1.28 (3H, m) Mass: 428.39 (M+1)

(1α,5α,6α)-N-(3-benzyl-3-azabicyclo[3.1.0]hex-6-yl-methyl)-2-hydroxy-2,2-di(4-fluorophenyl) acetic acid ester (Compound No. 37)

$^1$H-NMR (CDCl$_3$, 300 MHz) δ-values: 7.42-7.26 (9H, m), 6.99 (4H, m), 4.27 (1H, s), 4.11 (2H, d, 9 Hz), 3.57 (2H, s), 3.92 (2H, d, 9 Hz), 2.32 (2H, d, 9 Hz), 1.64-1.24 (3H, m)

(2R,2S)(1α,5α,6α)-(3-benzyl-3-azabicyclo[3.1.0]
hex-6-yl-methyl)-2-hydroxy-2-phenyl-2-(4-methylphenyl) acetic acid ester (Compound No. 43)

$^1$H-NMR (CDCl$_3$) δ-values: 7.46-7.43 (2H, m), 7.33-7.28 (10H, m), 7.12-7.10 (2H, m), 4.20 (1H, s), 4.11-4.08 (2H, m), 3.57 (2H, s), 2.92-2.89 (2H, m), 2.33-2.29 (5H, m), 1.31-1.28 (3H, m) Mass: 428.40 (M+1)

(2R,2S)(1α,5α,6α)-(3-benzyl-3-azabicyclo[3.1.0]
hex-6-yl-methyl)-2-hydroxy-2-methyl-2-phenyl acetic acid ester (Compound No. 44)

IR (DCM): 1726.3 cm$^{-1}$ $^1$H-NMR (CDCl$_3$) δ-values: 7.55-7.57 (m, 2H), 7.23-7.35 (m, 8H), 4.00 (d, J=9 Hz, 2H), 3.56 (s, 2H), 2.88-2.93 (m, 2H), 2.28-2.33 (m, 2H), 1.78 (s, 3H), 1.58-1.60 (m, 3H) Mass: 352 (M+1)

(2R,2S)(1α,5α,6α)-(3-benzyl-3-azabicyclo[3.1.0]
hex-6-yl-methyl)-2-hydroxy-2-isopropyl-2-phenyl acetic acid ester (Compound No. 46)

IR (DCM): 1721.4 cm$^{-1}$ $^1$H-NMR (CDCl$_3$) δ-values: 7.64-7.67 (m, 2H), 7.23-7.34 (m, 8H), 3.94-4.07 (m, 2H), 3.57 (s, 8H), 2.89-2.93 (m, 2H), 2.63 (m, 1H), 2.29-2.33 (m, 2H), 1.57-1.63 (m, 3H), 0.99 (d, J=6 Hz, 2H), 0.70 (d, J=6 Hz, 2H) Mass: 380 (M+1)

(2R,2S)(1α,5α,6α)(3-benzyl-3-azabicyclo[3.1.0] hex-6-yl-methyl]-2-hydroxy-2-(3-pentyl)-2-phenyl acetic acid ester (Compound No. 49)

IR (DCM): 1718.6 cm$^{-1}$ $^1$H-NMR (CDCl$_3$) δ-values: 7.65-7.68 (m, 2H), 7.23-7.34 (m, 8H), 3.94-4.05 (m, 2H), 3.70 (s, 1H), 3.58 (s, 2H), 2.90-2.94 (m, 2H), 2.31-2.33 (m, 2H), 2.25 (m, 1H), 1.62-1.64 (m, 3H), 1.19-1.32 (m, 4H), 0.98 (t, J=6 Hz, 3H), 0.72 (t, J=6 Hz, 3H) Mass: 408 (+1)

(2R,2S)(1α,5α,6α)-(3-benzyl-3-azabicyclo[3.1.0] hex-6-yl-methyl)-2-hydroxy-2-cyclopentyl-2-(3-methylphenyl) acetic acid ester (Compound No. 33)

EXAMPLE 4

Preparation of (2R,2S)(1α,5α,6α)-N-[3-(4-tert-butyl-benzyl)-3-azabicyclo[3.1.0]hex-6-yl-methyl]-2-hydroxy-2-cyclopentyl-2-phenylacetamide (Compound No. 14)

Step a: Preparation of (1α,5α,6α)-N-[3-benzyl-3-azabicyclo[3.1.0]hex-6-yl-methyl]-2-hydroxy-2-cyclopentyl-2-phenylacetamide This compound was prepared following the procedure described in Example 1.

Step b: Preparation of N-(3-azabicyclo[3.1.0]hex-6-ylmethyl)-2-cyclopentyl-2-hydroxy-2-phenylacetamide A solution of (1α,5α,6α)-N-[3-benzyl-3-azabicyclo [3.1.0]hex-6-yl-methyl]-2-hydroxy-2-cyclopentyl-2-phenylacetamide in methanol, containing ammonium formate (4.06 mmole), palladium on carbon (10% w/w) was heated at 80° C. for about 2 hours. The reaction mixture was filtered through celite bed and washed with methanol. The filtrate was evaporated under reduced pressure to get the desired compound.

Step c: Preparation of (2R,2S)(1α,5α,6α)-N-[3-(4-tert-butyl-benzyl)-3-azabicyclo[3.1.0]hex-6-yl-methyl]-2-hydroxy-2-cyclopentyl-2-phenylacetamide A solution of N-(3-azabicyclo[3.1.0]hex-6-ylmethyl)-2-cyclopentyl-2-hydroxy-2-phenylacetamide (1.59 mmole), 1-tert-butyl-4-chloromethyl-benzene (1.908 mmole) in dimethylformamide containing potassium carbonate (3.18 mmole) and potassium iodide (3.18 mmole) were stirred at room temperature overnight. The reaction mixture was poured into water and extracted with ethyl acetate. The organic layer was dried and concentrated under reduced pressure. The residue was purified by column chromatography eluting the compound with 25% ethyl acetate-hexane.

m. pt: 140-143° C. H$^1$-NMR (CDCl$_3$, 300 MHz) δ-values: 7.60 (2H, d, 6 Hz), 7.35-7.15 (7H, m), 6.41 (1H, bs, NH), 3.52 (2H, s), 3.19 (1H, bs), 3.03 (3H, m), 2.90 (2H, d, 9 Hz), 2.30 (2H, d, 9 Hz), 1.71-1.55 (9H, m), 1.25 (9H, s), 1.21 (2H, m) Mass: 461.7 (M+1)

Similarly, the following compound was prepared analogously, following the above procedure with appropriate substitution of reagents:

(2R,2S)(1α,5α,6α)-N-[3-(3-methylbenzyl)-3-azabicyclo[3.1.0]hex-6-yl-methyl]-2-hydroxy-2-cyclopentyl-2-phenylacetamide (Compound No. 24)

m. pt: 101.0-102.4° C. H$^1$-NMR (CDCl$_3$, 300 MHz) δ-values: 7.61-7.09 (9H, m) & 6.46 (1H, brs), 3.60-3.57 (2H, m), 3.16-2.98 (6H, m), 2.40-2.34 (4H, m), 1.65-1.41 (11H, m). Mass: 419.42 (M+1)

EXAMPLE 5

Preparation of (1α,5α,6α)-N-[3-(4-methylbenzyl)-3-azabicyclo[3.1.0]hex-6-yl-methyl]-2-hydroxy-2,2-diphenylacetamide (Compound No. 16)

Step a: Preparation of (1α,5α,6α)-N-[3-benzyl-3-azabicyclo[3.1.0]hex-6-yl-methyl]-2-hydroxy-2,2-diphenylacetamide This compound was prepared following the procedure described in Example 1.

Step b: Preparation of (3-azabicyclo[3.1.0]hex-6-ylmethyl)-2-hydroxy-2,2-diphenyl acetamide A solution of (1α,5α,6α)-N-[3-benzyl-3-azabicyclo [3.1.0]hex-6-yl-methyl]-2-hydroxy-2,2-diphenylacetamide in methanol, containing ammonium formate (4.06 mmole), palladium on carbon (10% w/w) was heated at 80° C. for about 2 hours. The reaction mixture was filtered through celite bed and washed with methanol. The filtrate was evaporated under reduced pressure to get the desired compound.

Step c: Preparation of (1α,5α,6α)-N-[3-(4-methylbenzyl)-3-azabicyclo[3.1.0]hex-6-yl-methyl]-2-hydroxy-2,2-diphenylacetamide To a stirred solution of (3-azabicyclo[3.1.0]hex-6-ylmethyl)-2-hydroxy-2,2-diphenyl acetamide (0.62 mmole) in acetonitrile were added p-methyl benzyl bromide (0.68 mmole) followed by potassium carbonate (1.6) and potassium iodide (0.62 mmole) and reaction mixture was refluxed for about 4½ hours and then at room temperature overnight. The reaction mixture was quenched by addition of water and organic layer extracted with ethyl acetate. The organic layer was washed with water brine, dried over anhydrous sodium sulphate, and then concentrated to get crude compound. Purification was done by column chromatography using dichloromethane, which was gradually changed to 2% methanol in dichloromethane.

IR: 3405, 1657.4 cm$^{-1}$ H$^1$-NMR (CDCl$_3$, 300 MHz) δ-values: 7.44-7.25 (10H, m), 7.12 (4H, m), 6.33 (1H, bs), 3.54 (2H, s), 3.15 (2H, t, 7.2 Hz), 2.94 (2H, d, 9 Hz), 2.33 (5H, s), 1.43 (2H, m), 0.88 (1H, m) Mass: 427.25 (M+1)

Similarly, the following compounds were prepared analogously, following the above procedures with appropriate substitution of reagents:

(2R,2S)(1α,5α,6α)-N-[3-(4-methylbenzyl)-3-azabicyclo[3.1.0]hex-6-yl-methyl]-2-hydroxy-2-cyclopentyl-2-phenylacetamide (Compound No. 17)

m. pt: 142.1-146.2° C. H$^1$-NMR (CDCl$_3$, 300 MHz) δ-values: 7.60 (2H, d, 6 Hz), 7.36-7.23 (3H, m), 7.16-7.09 (4H, m), 6.43 (1H, bs), 3.49 (2H, s), 3.19 (1H, bs), 3.04 (3H, m), 2.91 (2H, m), 2.33 (5H, s), 1.55-1.33 (11H, m), 0.88 (1H, m) Mass: 419.34 (M+1)

(2R,2S)(1α,5α,6α)-N-(3-cyclohexylmethyl-3-azabicyclo[3.1.0]hex-6-yl-methyl)-2-hydroxy-2-cyclopentyl-2-phenylacetamide (Compound No. 40)

$^1$H-NMR (CDCl$_3$) δ-values: 7.61-7.33 (5H, m), 6.41 (1H, brs), 3.20 (1H, s), 3.05-2.90 (5H, m), 2.21-2.15 (4H, m), 1.68-1.32 (22H, m) Mass: 411.33 (M+1)

(2R,2S)(1α,5α,6α)-N-{-[4-(1,3-dioxo-1,3-dihydro-isoindol-2-yl)-butyl]-3-azabicyclo[3.1.0]hex-6-yl-methyl}-2-hydroxy-2-cyclopentyl-2-phenylacetamide (Compound No. 1)

m.p: 113-114° C. IR (DCM): 1711.4, 1663.8 cm$^{-1}$ $_1$H-NMR (CDCl$_3$) δ-values: 7.83-7.85 (m, 2H), 7.72-7.73 (m, 2H), 7.59-7.62 (m, 2H), 7.32-7.36 (m, 3H), 6.41 (brs, 1H), 3.65-3.70 (m, 2H), 3.24 (s, 1H), 2.95-3.06 (m, 5H), 2.39-2.41 (m, 2H), 2.23-2.25 (m, 2H), 1.42-1.67 (m, 4H), 1.23-1.37 (m, 10H), 0.88 (m, Mass: 516 (M+1)

(2R,2S)(1α,5α,6α)-N-(3-Isopropyl-3-azabicyclo[3.1.0]hex-6-yl-methyl)-2-hydroxy-2-cyclopentyl-2-phenylacetamide (Compound No. 3)

IR (DCM): 1666.8 cm$^{-1}$ $^1$H-NMR (CDCl$_3$) δ-values: 7.60-7.63 (m, 2H), 7.32-7.37 (m, 3H), 6.99 (brs, 1H), 3.69 (m, 1H), 3.36-3.41 (m, 2H), 2.85 (m, 3H), 2.23-2.41 (m, 2H), 1.46-1.66 (m, 14H), 1.26 (s, 2H), 0.88 (m, 1H) Mass: 357 (M+1)

(2R,2S)(1α,5α,6α)-N-(3-Diphenylmethyl-3-azabicyclo[3.1.0]hex-6-yl-methyl)-2-hydroxy-2-cyclopentyl-2-phenylacetamide (Compound No. 4)

m.p: 161-163° C. IR (KBr): 1658.6 cm$^{-1}$ $^1$H-NMR (CDCl$_3$) δ-values: 7.89-7.91 (m, 4H), 7.56-7.80 (m, 5H), 7.16-7.43 (m, 6H), 6.88 (brs, 1H), 4.79-4.82 (m, 1H), 3.57-3.61 (m, 2H), 3.03-3.16 (m, 4H), 2.58 (brs, 1H), 1.11-1.62 (m, 11H) Mass: 481 (M+1)

(2R,2S)(1α,5α,6α)-N-(3-sec-butyl-3-azabicyclo[3.1.0]hex-6-yl-methyl)-2-hydroxy-2-cyclopentyl-2-phenylacetamide (Compound No. 5)

m.p: 109-110° C. IR (DCM): 1653.3 cm$^{-1}$ $^1$H-NMR (CDCl$_3$) δ-values: 7.59-7.62 (m, 2H), 7.24-7.37 (m, 3H), 6.39 (brs, 1H), 3.22 (s, 1H), 3.01-3.05 (m, 3H), 2.88-2.93 (m, 2H), 2.10-2.37 (m, 3H), 1.47-1.69 (m, 5H), 1.21-1.29 (m, 8H), 0.93-0.95 (m, 3H), 0.79-0.84 (m, 3H) Mass: 372 (M+2)

(1α,5α,6α)-N-(3-methyl-3-azabicyclo[3.1.0]hex-6-yl-methyl]-2-hydroxy-2-phenyl-(N-methyl)-2-phenylacetamide (Compound No. 47)

m. pt: 119.3-123.4° C. IR: 3061.2, 1637.2 cm$^{-1}$ $^1$H-NMR (CDCl$_3$, 300 MHz) δ-values: 7.33 (10H, bs), 6.06 (1H, bs), 3.42 (2H, bs), 2.98 (2H, m), 2.52 (3H, bs), 2.30 (6H, bs), 1.47-0.88 (3H, m)

(1α,5α,6α)-N-[3-(3-methylbenzyl)-3-azabicyclo[3.1.0]hex-6-yl-methyl]-2-hydroxy-2,2-diphenylacetamide (Compound No. 19)

m. pt: 111.2-112.6° C. H$^1$-NMR (CDCl$_3$, 300 MHz) δ-values: 7.44-7.26 (11H, m), 7.07 (3H, m), 6.5 (1H, bs), 3.59 (2H, bs), 3.17 (2H, t, 6 Hz), 2.98 (2H, m), 2.34 (5H, s), 1.49 (2H, bs), 0.88 (1H, m) Mass: 427.90 (M+1)

(1α,5α,6α)-N-[3-(3-fluorobenzyl)-3-azabicyclo[3.1.0]hex-6-yl-methyl]-2-hydroxy-2,2-diphenylacetamide (Compound No. 20)

m. pt: 107.8-108.4° C. H$^1$-NMR (CDCl$_3$, 300 MHz) δ-values: 7.44-7.2 (11H, m), 7.02-6.89 (3H, m), 6.36 (1H, bs), 3.56 (2H, s), 3.17 (3H, t, 6 Hz), 2.94 (2H, d, 9 Hz), 2.33 (2H, d, 9 Hz), 1.27 (2H, m), 0.88 (1H, m) Mass: 431.6 (M+1)

(2R,2S)(1α,5α,6α)-N-[3-(3-fluorobenzyl)-3-azabicyclo[3.1.0]hex-6-yl-methyl]-2-hydroxy-2-cyclohexyl-2-phenylacetamide (Compound No. 21)

m. pt: 99.5-101.8° C. H$^1$-NMR (CDCl$_3$, 300 MHz) δ-values: 7.60 (2H, d, 7.8 Hz), 7.36-7.19 (4H, m), 7.01-6.88 (3H, m), 6.64 (1H, bs), 3.54 (2H, s), 3.10-2.86 (5H, m), 2.40-2.28 (3H, m), 1.36-1.12 (12H, m), 0.88 (2H, m) Mass: 437.4 (M+1)

(2R,2S)(1α,5α,6α)-N-[2-(2,4-difluorobenzyl)-3-azabicyclo[3.1.0]hex-6-yl-methyl]-2-hydroxy-2-cyclohexyl-2-phenylacetamide (Compound No. 22)

m. pt: 98.2-100.4° C. H$^1$-NMR (CDCl$_3$, 300 MHz) δ-values: 7.61-7.31 (6H, m), 6.84-6.73 (2H, m), 6.64 (1H, brs), 3.58 (2H, s), 3.08-2.84 (6H, m), 1.69-1.21 (14H, m) Mass: 455.80 (M+1)

(1α,5α,6α)-N-[3-(2,4-difluorobenzyl)-3-azabicyclo[3.1.0]hex-6-yl-methyl]-2-hydroxy-2,2-diphenylacetamide (Compound No. 23)

m. pt: 116.3-116.9° C. IR (DCM): 1655.0 cm$^{-1}$ H$^1$-NMR (CDCl$_3$, 300 MHz) δ-values: 7.44-7.32 (11H, m), 6.82-6.79 (2H, m), 6.35 (1H, brs), 3.60 (1H, brs), 3.18-3.14 (2H, m), 3.01-2.98 (2H, m), 2.93-2.90 (2H, m), 2.38-2.35 (2H, m), 1.39-1.36 (3H, m) Mass: 449.200 (M+1)

EXAMPLE 6

Preparation of (2R,2S)(1α,5α,6α)-N-[3-(4-methylbenzyl)-3-azabicyclo[3.1.0]hex-6-yl-methyl]-2-hydroxy-2-cyclohexyl-2-phenylacetamide (Compound No. 18)

Step a: Preparation of (1α,5α,6α)-N-[3-benzyl-3-azabicyclo[3.1.0]hex-6-yl-methyl]-2-hydroxy-2-cyclohexyl-2-phenylacetamide This compound was prepared following the procedure described in Example 1.

Step b: Preparation of (3-azabicyclo[3.1.0]hex-6-ylmethyl)-2-cyclohexyl-2-hydroxy-2-phenyl acetamide A solution of (1α,5α,6α)-N-[3-benzyl-3-azabicyclo[3.1.0]hex-6-yl-methyl]-2-hydroxy-2-cyclohexyl-2-phenylacetamide in methanol, containing ammonium formate (4.06 mmole), palladium on carbon (10% w/w) was heated at 80° C. for about 2 hours. The reaction mixture was filtered through celite bed and washed with methanol. The filtrate was evaporated under reduced pressure to get the desired compound.

Step c: Preparation of (2R,2S)(1α,5α,6α)-N-[3-(4-methylbenzyl)-3-azabicyclo[3.1.0]hex-6-yl-methyl]-2-hydroxy-2-cyclohexyl-2-phenylacetamide To a solution of (3-azabicyclo[3.1.0]hex-6-ylmethyl)-2-cyclohexyl-2-hydroxy-2-phenyl acetamide (1 mmole) in tetrahydrofuran p-methylbenzaldehyde (2.9 mmole) was added followed by hydride [NaB(OAC)$_3$H] reagent. The white suspension was stirred at room temperature overnight, then quenched by addition of aqueous sodium bicarbonate solution and extracted with ethyl acetate. The organic layer was washed with brine, dried and evaporated to give crude mixture. This was purified by column chromatography using silica gel with dichloromethane and 2% methanol in dichloromethane.

H$^1$-NMR (CDCl$_3$, 300 MHz) δ-values: 7.60 (2H, d, 7.5 Hz), 7.36-7.26 (3H, m), 7.11 (4H, bs), 6.61 (1H, bs), 3.52 (2H, s), 3.06-2.83 (4H, m), 2.39-2.28 (5H, m), 1.41-0.88 (14H, m) Mass: 433.8 (M+1)

EXAMPLE 7

Preparation of (2R,2S)(1α,5α,6α)-(3-benzyl-3-azabicyclo[3.1.0]hex-6-yl-methyl)-2-hydroxy-2-cyclopentyl-2-(3-methylphenyl) acetic acid ester tartarate salt (Compound No. 34)

L-(+)-Tartaric acid (0.322 mmole) was added to the solution of (1α,5α,6α)-(3-benzyl-3-azabicyclo[3.1.0]hex-6-yl-methyl)-2-hydroxy-2-cyclopentyl-2-(3-methylphenyl) acetate (prepared following the procedure described in Example 1) in ethanol (0.322 mmole) and heated at 60° C. for about half an hour. The reaction mixture was concentrated under reduced pressure. Ether was added to the reaction mixture. The ethereal layer was decanted off and residue dried.

H$^1$-NMR (CDCl$_3$, 300 MHz) δ-values: 7.38-7.33 (7H, m), 7.12 (1H, m), 6.98 (1H, m), 4.39 (2H, s), 4.07-3.98 (3H, m), 3.26-3.10 (5H, m), 1.59-1.41 9H, m), 1.26 (3H, m)

EXAMPLE 8

Preparation of (2R,2S)(1α,5α,6α)-N-(3-benzyl-3-azabicyclo[3.1.0]hex-6-yl-methyl)-2-hydroxy-2-cyclopentyl-2-(3-methylphenyl)acetamide tartarate salt (Compound No. 36)

L-(+)-Tartarate salt was prepared following the procedure described in Example 9 using (1α,5α,6α)-N-(3-benzyl-3-azabicyclo[3.1.0]hex-6-yl-methyl)-2-hydroxy-2-cyclopentyl-2-(3-methylphenyl)acetamide (prepared following the procedure described in Example 1)

H$^1$-NMR (CDCl$_3$, 300 MHz) δ-values: 7.42-7.34 (7H, m), 7.21 (1H, m), 6.99 (1H, m), 4.41 (2H, s), 4.19 (2H, s), 3.03 (3H, bs), 2.26 (3H, s), 1.59-1.27 (10H, m), 1.17 (2H, m)

Biological Activity

Radioligand Binding Assays:

The affinity of test compounds for $M_2$ and $M_3$ muscarinic receptor subtypes was determined by [$^3$H]-N-methylscopolamine binding studies using rat heart and submandibular gland respectively as described by Moriya et al., (Life Sci, 1999, 64(25):2351-2358) with minor modifications.

Membrane preparation: Submandibular glands and heart were isolated and placed in ice cold homogenising buffer (HEPES 20 mM, 10 mM EDTA, pH 7.4) immediately after sacrifice. The tissues were homogenised in 10 volumes of homogenising buffer and the homogenate was filtered through two layers of wet gauze and filtrate was centrifuged at 500 g for 10 min. The supernatant was subsequently centrifuged at 40,000 g for 20 min. The pellet thus obtained was resuspended in same volume of assay buffer (HEPES 20 mM, EDTA 5 mM, pH 7.4) and were stored at −70° C. until the time of assay.

Ligand binding assay: The compounds were dissolved and diluted in DMSO. The membrane homogenates (150-250 μg protein) were incubated in 250 μl of assay buffer (HEPES 20 mM, pH 7.4) at 24-25° C. for 3 h. Non-specific binding was determined in the presence of 1 μM atropine. The incubation was terminated by vacuum filtration over GF/B fiber filters (Wallac). The filters were then washed with ice cold 50 mM Tris HCl buffer (pH 7.4). The filter mats were dried and bound radioactivity retained on filters was counted. The IC$_{50}$ & Kd were estimated by using the non-linear curve fitting program using G Pad Prism software. The value of inhibition constant Ki was calculated from competitive binding studies by using Cheng & Prusoff equation (*Biochem Pharmacol*, 1973, 22: 3099-3108), Ki=IC$_{50}$/(1+L/Kd), where L is the concentration of [$^3$H] NMS used in the particular experiment.

The K$_i$ results of the compounds observed were in the range of 2 nM to 1122 nM for $M_2$ receptor and 0.1 nM to >1000 for $M_3$ receptor.

Functional Experiments Using Isolated Rat Bladder:

Methodology:

Animals are euthanized by overdose of urethane and whole bladder is isolated and removed rapidly and placed in ice cold Tyrode buffer with the following composition (mMol/L) NaCl 137; KCl 2.7; CaCl$_2$ 1.8; MgCl$_2$ 0.1; NaHCO$_3$ 11.9; NaH$_2$PO$_4$ 0.4; Glucose 5.55 and continuously gassed with 95% O$_2$ and 5% CO$_2$.

The bladder is cut into longitudinal strips (3 mm wide and 5-6 mm long) and mounted in 10 ml organ baths at 30° C., with one end connected to the base of the tissue holder and the other end connected to a polygraph through a force displacement transducer. Each tissue is maintained at a constant basal tension of 2 g and allowed to equilibrate for 1 hour during which the Physiological Salt Solution (PSS) is changed every 15 min. At the end of equilibration period the stabilization of the tissue contractile response is assessed with 1 mmol/L of Carbachol consecutively for 2-3 times. Subsequently a cumulative concentration response curve to carbachol (10$^{-9}$ mol/L to 3×10$^{-5}$ mol/L) is obtained. After several washes, once the baseline is achieved, cumulative concentration response curve is obtained in presence of New Chemical Entity (NCE) [NCE added 20 min. prior to the second Cumulative Response Curve (CRC)].

The contractile results are expressed as % of control E max. ED$_{50}$ values are calculated by fitting a non-linear regression curve (Graph Pad Prism). pKB values are calculated by the formula pKB=−log [(molar concentration of antagonist/(dose ratio−1))]

where, dose ratio=ED$_{50}$ in the presence of antagonist/ED$_{50}$ in the absence of antagonist.

In Vivo Experiments Using Anaesthetized Rabbit

Methodology

Male rabbits are anaesthetized with urethane 1.5 g/kg intravenously. Trachea is cannulated to maintain the patency of airway. Femoral vein and femoral arteries of both sides are cannulated for the administration of vehicle or drug substances for the measurement of BP and administration of carbachol intra-arterially respectively.

Polyethylene tubing is introduced into the bladder through the urethra and tied at the neck of the bladder. The other end of the catheter is connected to the Grass polygraph through a Statham pressure transducer. The bladder is filled with warm (37° C.) saline. Both the ureters are ligated and cut proximally to drain the urine coming from kidneys. A stabilization period of 30-60 is allowed for stabilization of parameters from surgical procedures.

Salivary response is assessed by measuring the weight of a preweighted cotton gauze kept for 2 minutes in the buccal cavity immediately after the carbachol challenge.

At the end of stabilization period 2 control responses to carbachol (1.5 µg/kg intra-arterial) on bladder pressure and salivation are obtained and this response is considered as 100%. Subsequently, the effect of increasing dose of NCE (ranging from 3 µg/kg to 1 mg/kg) or vehicle (i.v., 15 min before carbachol challenge) is examined.

The change in bladder pressure and salivation are expressed as % change from pretreatment control averages. The $ID_{50}$ values for salivation and bladder pressure inhibition are calculated at dose using Graph Pad Prism software, by fitting the values at dose into non-linear regression curve. Oxybutynin and Tolterodine are used as standards for comparison.

The bladder selectivity to salivation is calculated by using following formula and expressed as fold of selectivity of oxybutinin in the same model.

$$\frac{ID_{50} \text{Salivary response}}{ID_{50} \text{Bladder pressure}}$$

While the present invention has been described in terms of its specific embodiments, certain modifications and equivalents will be apparent to those skilled in the art and are intended to be included within the scope of the present invention.

We claim:

1. A compound selected from:
   (2R,2S)(1α,5α,6α)-N-{-[4-(1,3-dioxo-1,3-dihydro-isoindol-2-yl)-butyl]-3-azabicyclo[3.1.0]hex-6-yl-methyl}-2-hydroxy-2-cyclopentyl-2-phenylacetamide (Compound No. 1);
   (2R)(1α,5α,6α)-N-(3-Benzyl-3-azabicyclo[3.1.0]hex-6-yl-methyl)-2-hydroxy-2-cyclopent-1-enyl-2-phenylacetamide (Compound No. 2);
   (2R,2S)(1α,5α,6α)-N-(3-Isopropyl-3-azabicyclo[3.1.0]hex-6-yl-methyl)-2-hydroxy-2-cyclopentyl-2-phenylacetamide (Compound No. 3);
   (2R,2S)(1α,5α,6α)-N-(3-Diphenylmethyl-3-azabicyclo[3.1.0]hex-6-yl-methyl)-2-hydroxy-2-cyclopentyl-2-phenylacetamide (Compound No. 4);
   (2R,2S)(1α,5α,6α)-N-(3-sec-butyl-3-azabicyclo[3.1.0]hex-6-yl-methyl)-2-hydroxy-2-cyclopentyl-2-phenylacetamide (Compound No. 5);
   (2R,2S)(1α,5α,6α)-N-(3-Benzyl-3-azabicyclo[3.1.0]hex-6-yl-methyl)-2-hydroxy-2-(3-pentyl)-2-phenylacetamide (Compound No. 6);
   (2R,2S)(1α,5α,6α)-N-(3-Benzyl-3-azabicyclo[3.1.0]hex-6-yl-methyl)-2-hydroxy-2-cyclohexyl-2-(4-methoxyphenyl)acetamide (Compound No. 7);
   (2R,2S)(1α,5α,6α)-N-(3-Benzyl-3-azabicyclo[3.1.0]hex-6-yl-methyl)-2-hydroxy-2-phenyl-(N-ethyl)-2-phenylacetamide (Compound No. 8);
   (2R,2S)(1α,5α,6α)-N-(3-Benzyl-3-azabicyclo[3.1.0]hex-6-yl-methyl)-2-hydroxy-2-cyclopentyl-(N-ethyl)-2-phenylacetamide (Compound No. 9);
   (2R,2S)(1α,5α,6α)-N-(3-Benzyl-3-azabicyclo[3.1.0]hex-6-yl-methyl)-2-hydroxy-2-cyclohexyl-(N-ethyl)-2-phenylacetamide (Compound No. 10);
   (2R,2S)(1α,5α,6α)-N-(3-Benzyl-3-azabicyclo[3.1.0]hex-6-yl-methyl)-2-hydroxy-2-(3-pentyl)-(N-methyl)-2-phenylacetamide (Compound No. 11);
   (2R,2S)(1α,5α,6α)-N-(3-Benzyl-3-azabicyclo[3.1.0]hex-6-yl-methyl)-2-hydroxy-2-(sec-butyl)-(N-methyl)-2-phenylacetamide (Compound No. 12);
   (2R,2S)(1α,5α,6α)-N-(3-Benzyl-3-azabicyclo[3.1.0]hex-6-yl-methyl)-2-hydroxy-2-isopropyl-(N-methyl)-2-phenylacetamide (Compound No. 13);
   (2R,2S)(1α,5α,6α)-N-[3-(4-tert-butyl-benzyl)-3-azabicyclo[3.1.0]hex-6-yl-methyl]-2-hydroxy-2-cyclopentyl-2-phenylacetamide (Compound No. 14);
   (2R,2S)(1α,5α,6α)-N-(3-Benzyl-3-azabicyclo[3.1.0]hex-6-yl-methyl)-2-hydroxy-2-cyclohex-2-enyl-2-phenylacetamide (Compound No. 15);
   (2R,2S)(1α,5α,6α)-N-[3-(4-methylbenzyl)-3-azabicyclo[3.1.0]hex-6-yl-methyl]-2-hydroxy-2,2-diphenylacetamide (Compound No. 16);
   (2R,2S)(1α,5α,6α)-N-[3-(4-methylbenzyl)-3-azabicyclo[3.1.0]hex-6-yl-methyl]-2-hydroxy-2-cyclopentyl-2-phenylacetamide (Compound No. 17);
   (2R,2S)(1α,5α,6α)-N-[3-(4-methylbenzyl)-3-azabicyclo[3.1.0]hex-6-yl-methyl]-2-hydroxy-2-cyclohexyl-2-phenylacetamide (Compound No. 18);
   (2R,2S)(1α,5α,6α)-N-[3-(3-methylbenzyl)-3-azabicyclo[3.1.0]hex-6-yl-methyl]-2-hydroxy-2,2-diphenylacetamide (Compound No. 19);
   (2R,2S)(1α,5α,6α)-N-[3-(3-fluorobenzyl)-3-azabicyclo[3.1.0]hex-6-yl-methyl]-2-hydroxy-2,2-diphenylacetamide (Compound No. 20);
   (2R,2S)(1α,5α,6α)-N-[3-(3-fluorobenzyl)-3-azabicyclo[3.1.0]hex-6-yl-methyl]-2-hydroxy-2-cyclohexyl-2-phenylacetamide (Compound No. 21);
   (2R,2S)(1α,5α,6α)-N-[2-(2,4-difluorobenzyl)-3-azabicyclo[3.1.0]hex-6-yl-methyl]-2-hydroxy-2-cyclohexyl-2-phenylacetamide (Compound No. 22);
   (2R,2S)(1α,5α,6α)-N-[3-(2,4-difluorobenzyl)-3-azabicyclo[3.1.0]hex-6-yl-methyl]-2-hydroxy-2,2-diphenylacetamide (Compound No. 23);
   (2R,2S)(1α,5α,6α)-N-[3-(3-methylbenzyl)-3-azabicyclo[3.1.0]hex-6-yl-methyl]-2-hydroxy-2-cyclopentyl-2-phenylacetamide (Compound No. 24);
   (2R,2S)(1α,5α,6α)-N-(3-benzyl-3-azabicyclo[3.1.0]hex-6-yl-methyl)-2-hydroxy-2-(4-methylphenyl)-2-phenylacetamide (Compound No. 25);
   (2R,2S)(1α,5α,6α)-N-(3-benzyl-3-azabicyclo[3.1.0]hex-6-yl-methyl)-2-hydroxy-2-(4-methylphenyl)-(N-methyl)-2-phenylacetamide (Compound No. 26);
   (2R,2S)(1α,5α,6α)-N-(3-benzyl-3-azabicyclo[3.1.0]hex-6-yl-methyl)-2-hydroxy-2-(4-fluorophenyl)-2-phenylacetamide (Compound No. 27);
   (2R,2S)(1α,5α,6α)-(3-benzyl-3-azabicyclo[3.1.0]hex-6-yl-methyl)-2-hydroxy-2-(4-fluorophenyl)-2-phenyl acetic acid ester (Compound No. 28);
   (2R,2S)(1α,5α,6α)-N-(3-benzyl-3-azabicyclo[3.1.0]hex-6-yl-methyl)-2-hydroxy-2-(4-fluorophenyl)-(N-methyl)-2-phenylacetamide (Compound No. 29);
   (2R,2S)(1α,5α,6α)-N-(3-benzyl-3-azabicyclo[3.1.0]hex-6-yl-methyl)-2-hydroxy-2-(3-methylphenyl)-2-phenylacetamide (Compound No. 30);

(2R,2S)(1α,5α,6α)-N-(3-benzyl-3-azabicyclo[3.1.0]hex-6-yl-methyl)-2-hydroxy-2-(3-methylphenyl)-(N-methyl)-2-phenylacetamide (Compound No. 31);

(2R,2S)(1α,5α,6α)-(3-benzyl-3-azabicyclo[3.1.0]hex-6-yl-methyl)-2-hydroxy-2-(3-methylphenyl)-2-phenyl acetic acid ester (Compound No. 32);

(2R,2S)(1α,5α,6α)-(3-benzyl-3-azabicyclo[3.1.0]hex-6-yl-methyl)-2-hydroxy-2-cyclopentyl-2-(3-methylphenyl) acetic acid ester (Compound No. 33);

(2R,2S)(1α,5α,6α)-(3-benzyl-3-azabicyclo[3.1.0]hex-6-yl-methyl)-2-hydroxy-2-cyclopentyl-2-(3-methylphenyl) acetic acid ester tartarate salt (Compound No. 34);

(2R,2S)(1α,5α,6α)-N-(3-benzyl-3-azabicyclo[3.1.0]hex-6-yl-methyl)-2-hydroxy-2-cyclopentyl-2-(3-methylphenyl)acetamide (Compound No. 35);

(2R,2S)(1α,5α,6α)-N-(3-benzyl-3-azabicyclo[3.1.0]hex-6-yl-methyl)-2-hydroxy-2-cyclopentyl-2-(3-methylphenyl)acetamide tartarate salt (Compound No. 36);

(2R,2S)(1α,5α,6α)-N-(3-benzyl-3-azabicyclo[3.1.0]hex-6-yl-methyl)-2-hydroxy-2,2-di(4-fluorophenyl)acetic acid ester (Compound No. 37);

(2R,2S)(1α,5α,6α)-N-(3-benzyl-3-azabicyclo[3.1.0]hex-6-yl-methyl]-2-hydroxy-2,2-di(4-fluorophenyl)-acetamide (Compound No. 38);

(2R,2S)(1α,5α,6α)-(3-benzyl-3-azabicyclo[3.1.0]hex-6-yl-methyl]-2-hydroxy-2-cyclobutyl-2-phenyl acetic acid ester (Compound No. 39);

(2R,2S)(1α,5α,6α)-N-(3-cyclohexylmethyl-3-azabicyclo[3.1.0]hex-6-yl-methyl)-2-hydroxy-2-cyclopentyl-2-phenylacetamide (Compound No. 40);

(2R)(1α,5α,6α)-N-(3-benzyl-3-azabicyclo[3.1.0]hex-6-yl-methyl)-2-hydroxy-2-cyclopentyl-(N-methyl)-2-phenylacetamide (Compound No. 41);

(2R,2S)(1α,5α,6α)-N-(3-benzyl-3-azabicyclo[3.1.0]hex-6-yl-methyl]-2-hydroxy-2-cyclopentyl-2-(4-methylphenyl)acetamide (Compound No. 42);

(2R,2S)(1α,5α,6α)-(3-benzyl-3-azabicyclo[3.1.0]hex-6-yl-methyl)-2-hydroxy-2-phenyl-2-(4-methylphenyl) acetic acid ester (Compound No. 43);

(2R,2S)(1α,5α,6α)-(3-benzyl-3-azabicyclo[3.1.0]hex-6-yl-methyl)-2-hydroxy-2-methyl-2-phenyl acetic acid ester (Compound No. 44);

(2R,2S)(1α,5α,6α)-N-(3-benzyl-3-azabicyclo[3.1.0]hex-6-yl-methyl]-2-hydroxy-2-methyl-2-phenyl acetamide (Compound No. 45);

(2R,2S)(1α,5α,6α)-(3-benzyl-3-azabicyclo[3.1.0]hex-6-yl-methyl)-2-hydroxy-2-isopropyl-2-phenyl acetic acid ester (Compound No. 46);

(2R,2S)(1α,5α,6α)-N-(3-methyl-3-azabicyclo[3.1.0]hex-6-yl-methyl]-2-hydroxy-2-phenyl-(N-methyl)-2-phenylacetamide (Compound No. 47);

(2R,2S)(1α,5α,6α)-N-(3-benzyl-3-azabicyclo[3.1.0]hex-6-yl-methyl]-2-hydroxy-2-(3-methylphenyl)-2-(3-methylphenyl)acetamide (Compound No. 48);

(2R,2S)(1α,5α,6α)-(3-benzyl-3-azabicyclo[3.1.0]hex-6-yl-methyl]-2-hydroxy-2-(3-pentyl)-2-phenyl acetic acid ester (Compound No. 49); and (2R,2S)(1α,5α,6α)-N-(3-benzyl-3-azabicyclo[3.1.0]hex-6-yl-methyl)-2-hydroxy-2-methyl-(N-methyl)-2-phenylacetamide (Compound No. 50).

2. A pharmaceutical composition comprising a therapeutically effective amount of a compound as defined in claim 1 together with pharmaceutically acceptable carriers, excipients or diluents.

* * * * *